US012121219B2

(12) United States Patent
Kono et al.

(10) Patent No.: US 12,121,219 B2
(45) Date of Patent: Oct. 22, 2024

(54) MEDICAL IMAGE PROCESSING DEVICE, MEDICAL IMAGING DEVICE, MEDICAL OBSERVATION SYSTEM, IMAGE PROCESSING METHOD, AND COMPUTER-READABLE RECORDING MEDIUM

(71) Applicant: OLYMPUS CORPORATION, Tokyo (JP)

(72) Inventors: Hidetaro Kono, Hachioji (JP); Yutaka Koyama, Kawasaki (JP); Kotaro Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 101 days.

(21) Appl. No.: 17/903,195

(22) Filed: Sep. 6, 2022

(65) Prior Publication Data
US 2023/0000329 A1    Jan. 5, 2023

Related U.S. Application Data

(63) Continuation of application No. PCT/JP2020/010105, filed on Mar. 9, 2020.

(51) Int. Cl.
*A61B 1/06* (2006.01)
*A61B 1/04* (2006.01)
*A61B 1/00* (2006.01)

(52) U.S. Cl.
CPC ............... *A61B 1/06* (2013.01); *A61B 1/043* (2013.01); *A61B 1/00186* (2013.01)

(58) Field of Classification Search
CPC .......... A61B 1/000095; A61B 1/00186; A61B 1/043; A61B 1/044; A61B 1/045;
(Continued)

(56) References Cited

U.S. PATENT DOCUMENTS

| 5,749,830 A | 5/1998 | Kaneko et al. |
| 2002/0138008 A1* | 9/2002 | Tsujita ............... A61B 1/05 600/476 |

(Continued)

FOREIGN PATENT DOCUMENTS

| JP | H07155292 A | 6/1995 |
| JP | 2003-528 A | 1/2003 |

(Continued)

OTHER PUBLICATIONS

International Search Report dated May 26, 2020 issued in PCT/JP2020/010105.

*Primary Examiner* — Sherrie Hsia
(74) *Attorney, Agent, or Firm* — Scully, Scott, Murphy & Presser, P.C.

(57) ABSTRACT

A medical image processing device includes a processor configured to: obtain image data; generate, based on the obtained image data, a captured image including color component signals including a red component signal representing a red component, a green component signal representing a green component, and a blue component signal representing a blue component; calculate an intensity ratio between a fluorescent component signal and a reflected light component signal in a pixel of the captured image; determine, based on the calculated intensity ratio in the pixel of the captured image, a fluorescence region and a background region in the captured image; and generate a fluorescence image by performing, based on a result of the determination, image processing with parameters different from each other for color component signals in pixels positioned in the fluorescence region and color component signals in pixels positioned in the background region.

20 Claims, 20 Drawing Sheets

(58) Field of Classification Search
CPC ......... A61B 1/06; A61B 1/063; A61B 1/0638; H04N 23/12; H04N 23/55; H04N 23/555; H04N 23/56
USPC ........................ 348/446, 65, 69, 71; 382/128
See application file for complete search history.

(56) References Cited

U.S. PATENT DOCUMENTS

| 2003/0078477 A1 | 4/2003 | Kang et al. |
| 2023/0000330 A1* | 1/2023 | Igarashi ........... A61B 1/000095 |

FOREIGN PATENT DOCUMENTS

| JP | 2006020727 A | 1/2006 |
| JP | 2018126174 A | 8/2018 |

* cited by examiner

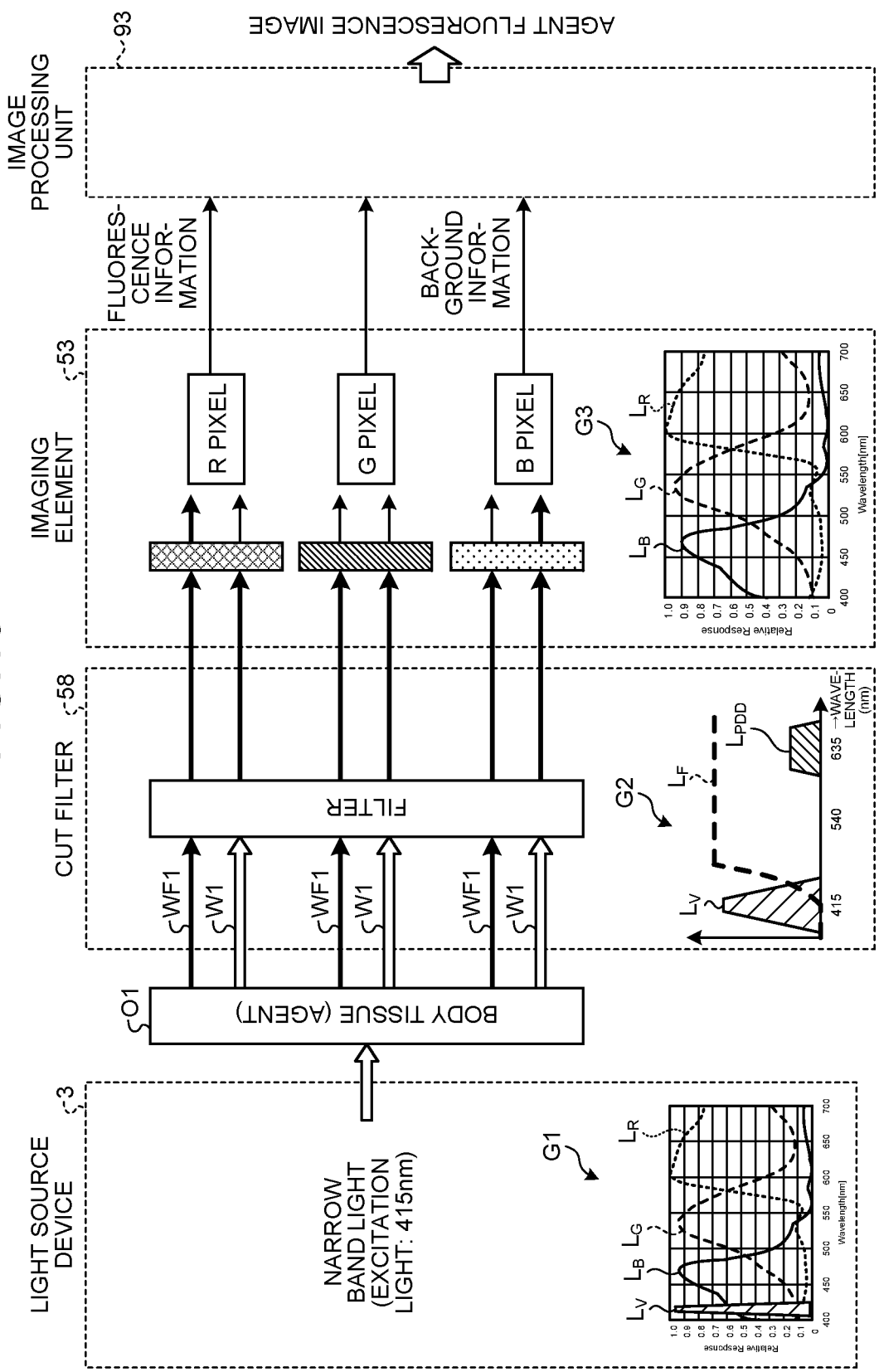

MEDICAL IMAGE PROCESSING DEVICE, MEDICAL IMAGING DEVICE, MEDICAL OBSERVATION SYSTEM, IMAGE PROCESSING METHOD, AND COMPUTER-READABLE RECORDING MEDIUM

CROSS-REFERENCE TO RELATED APPLICATION

This application is a continuation of International Application No. PCT/JP2020/010105, filed on Mar. 9, 2020, the entire contents of which are incorporated herein by reference.

BACKGROUND

1. Technical Field

The present disclosure relates to a medical image processing device, a medical imaging device, a medical observation system, an image processing method, and a computer-readable recording medium for implementing image processing of image data generated by imaging of a subject.

2. Related Art

In the related art, fluorescence observation and visible light observation are performed by provision of a filter on an incident side of an imaging element. This filter shields excitation light and transmits therethrough wavelengths of fluorescence (see, for example, Japanese Patent Application Laid-open No. 2006-020727). In this technique, fluorescence observation and visible light observation are performed by means of a single imaging element, by: rotation of a rotating plate arranged on an optical path of white light emitted by a lamp; and emission of excitation light and white light that are switched between each other, the rotating plate having a visible light illumination filter and an excitation light irradiation filter, the excitation light being for fluorescence observation, the white light being for visible light observation.

SUMMARY

In some embodiments, a medical image processing device includes a processor comprising hardware, the processor being configured to: obtain image data generated by imaging of reflected light and fluorescence, the reflected light being from body tissue irradiated with narrow band light, the fluorescence being from an observation target that emits fluorescence by irradiation of the body tissue with the narrow band light; generate, based on the obtained image data, a captured image including color component signals including a red component signal representing a red component, a green component signal representing a green component, and a blue component signal representing a blue component; calculate an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light; determine, based on the calculated intensity ratio in the pixel of the captured image, a fluorescence region and a background region in the captured image; and generate a fluorescence image by performing, based on a result of the determination, image processing with parameters different from each other for color component signals in pixels positioned in the fluorescence region and color component signals in pixels positioned in the background region.

In some embodiments, a medical imaging device includes: an imaging element including a pixel portion including plural pixels arranged in a two-dimensional matrix, and a color filter including red filters, green filters, and blue filters that are provided on light receiving surfaces of the plural pixels, each of the light receiving surfaces including any one filter of the red, green, and blue filters on plural pixels, each of the light receiving surfaces; an optical system configured to forms a subject image on a light receiving surface of the imaging element; and a cut filer provided on an optical path of the imaging element and optical system, the imaging element being configured to generate image data by imaging at least one of: reflected light from body tissue irradiated with narrow band light shorter in wavelength; and fluorescence from an advanced glycation end product produced by performing a heat treatment on the body tissue, the cut filter being configured to shield part of light of a shorter wavelength band including a wavelength band of the narrow band light, and transmit therethrough light of a wavelength band longer than a wavelength band of the light that is shielded.

In some embodiments, a medical observation system includes: a light source configured to emit narrow band light; a medical imaging device configured to generate image data; and a medical image processing device comprising a processor comprising hardware, the processor being configured to: obtain image data generated by imaging of reflected light and fluorescence, the reflected light being from body tissue irradiated with narrow band light, the fluorescence being from an observation target that emits fluorescence by irradiation of the body tissue with the narrow band light; generate, based on the obtained image data, a captured image including color component signals including a red component signal representing a red component, a green component signal representing a green component, and a blue component signal representing a blue component; calculate an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light; determine, based on the calculated intensity ratio in the pixel of the captured image, a fluorescence region and a background region in the captured image; and generate a fluorescence image by performing, based on a result of the determination, image processing with parameters different from each other for color component signals in pixels positioned in the fluorescence region and color component signals in pixels positioned in the background region.

In some embodiments, an image processing method includes: obtaining image data generated by imaging of reflected light and fluorescence, the reflected light being from body tissue irradiated with narrow band light, the fluorescence being from an observation target that emits fluorescence by irradiation of the body tissue with the narrow band light; generating, based on the obtained image data, a captured image including color component signals including a red component signal representing a red component, a green component signal representing a green component, and a blue component signal representing a blue component; calculating an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light; determining, based on the calculated intensity ratio in the pixel of the captured image, a fluorescence region and a background region in the captured image; and generating a fluorescence image by performing, based on a result of the determining, image processing with parameters different from each other for color component signals in pixels positioned in the fluorescence region and color component signals in pixels positioned in the background region.

In some embodiments, provided is a non-transitory computer-readable recording medium with an executable program stored thereon. The program causes a medical image processing device to: obtain image data generated by imaging of reflected light and fluorescence, the reflected light being from body tissue irradiated with narrow band light, the fluorescence being from an observation target that emits fluorescence by irradiation of the body tissue with the narrow band light; generate, based on the obtained image data, a captured image including color component signals including a red component signal representing a red component, a green component signal representing a green component, and a blue component signal representing a blue component; calculate an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light; determine, based on the calculated intensity ratio in the pixel of the captured image, a fluorescence region and a background region in the captured image; and generate a fluorescence image by performing, based on a result of the determination, image processing with parameters different from each other for color component signals in pixels positioned in the fluorescence region and color component signals in pixels positioned in the background region.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 16 is a diagram schematically illustrating principles of observation in an agent fluorescence observation mode according to the second embodiment;

DETAILED DESCRIPTION

Modes for implementing the present disclosure will hereinafter be described in detail, together with the drawings. The present disclosure is not limited by the following embodiments. Furthermore, the drawings referred to in the following description schematically depict shapes, sizes, and positional relations merely to an extent that allows substance of the present disclosure to be understood. That is, the present disclosure is not limited only to the shapes, sizes, and positional relations exemplified by the drawings. In addition, any portions that are the same will be assigned with the same reference sign throughout the drawings. An endoscope system including a rigid endoscope and a medical imaging device will be described as an example of a medical observation system according to the present disclosure.

First Embodiment

Configuration of Endoscope System

Figure 1:
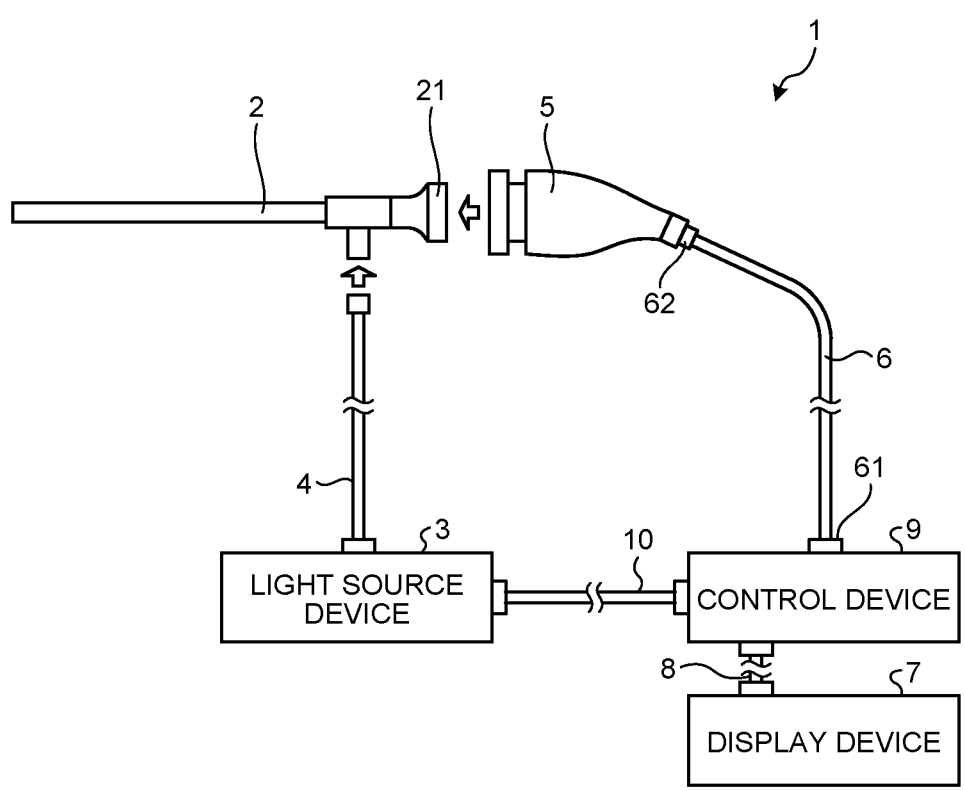
FIG. 1 is a diagram illustrating a schematic configuration of an endoscope system according to a first embodiment.

FIG. 1 is a diagram illustrating a schematic configuration of an endoscope system according to a first embodiment. An endoscope system 1 illustrated in FIG. 1 is a system that is used in the medical field and is for observation of body tissue in a subject, such as an organism. For this first embodiment, a rigid endoscope system using a rigid endoscope (an insertion portion 2) illustrated in FIG. 1 will be described as the endoscope system 1, but without being limited to the rigid endoscope system, the endoscope system 1 may be, for example, an endoscope system including a flexible endoscope. The endoscope system 1 may also be a medical microscope system including a medical imaging device that captures an image of a subject and where surgery or treatment is conducted while a display image based on image data captured by this medical imaging device is being displayed by a display device.

The endoscope system 1 illustrated in FIG. 1 is used when photodynamic diagnosis (PDD) observation is conducted for an observation target in body tissue of a subject, the observation target having been subjected to treatment, such as administration of a photosensitive substance, such as 5-aminolevulinic acid (hereinafter, referred to as "5-ALA"). Furthermore, the endoscope system 1 illustrated in FIG. 1 is used when surgery or treatment of a subject is conducted by use of a treatment tool (not illustrated in the drawings), such as an electrosurgical knife or an energy device, which enables heat treatment.

The endoscope system 1 illustrated in FIG. 1 includes the insertion portion 2, a light source device 3, a light guide 4, an endoscope camera head 5 (an imaging device for an endoscope), a first transmission cable 6, a display device 7, a second transmission cable 8, a control device 9, and a third transmission cable 10.

The insertion portion 2 is rigid or at least a part of the insertion portion 2 is flexible, and the insertion portion 2 has an elongated shape. The insertion portion 2 is inserted into a subject, such as a patient, via a trocar. The insertion portion 2 has, provided therein, an optical system, such as a lens, that forms an observation image.

One end of the light guide 4 is connected to the light source device 3, and the light source device 3 supplies, under control by the control device 9, illumination light to be emitted to the interior of a subject, to that one end of the light guide 4. The light source device 3 is implemented by use of: any one or more selected from a group of a light emitting diode (LED) light source, a xenon lamp, and a semiconductor laser element, such as a laser diode (LD); a processor that is a processing device having hardware, such as a field programmable gate array (FPGA) or a central processing unit (CPU); and a memory that is a transitory storage area used by the processor. The light source device 3 and the control device 9 may be configured to perform communication individually as illustrated in FIG. 1 or may be configured to be integrated with each other.

The one end of the light guide 4 is detachably connected to the light source device 3 and the other end of the light guide 4 is detachably connected to the insertion portion 2. The light guide 4 guides the illumination light supplied from the light source device 3 to the other end from the one end, to supply the illumination light to the insertion portion 2.

An eyepiece unit 21 of the insertion portion 2 is detachably connected to the endoscope camera head 5. Under control by the control device 9, the endoscope camera head 5 generates image data (RAW data) by receiving an observation image formed by the insertion portion 2 and performing photoelectric conversion of the observation image, and outputs the image data to the control device 9 via the first transmission cable 6.

One end of the first transmission cable 6 is detachably connected to the control device 9 via a video connector 61, and the other end of the first transmission cable 6 is detachably connected to the endoscope camera head 5 via a camera head connector 62. The first transmission cable 6 transmits the image data output from the endoscope camera head 5 to the control device 9 and transmits, for example, electric power and setting data output from the control device 9, to the endoscope camera head 5. The setting data include a control signal, a synchronization signal, and a clock signal for controlling the endoscope camera head 5.

Under control by the control device 9, the display device 7 displays a display image based on image data that have been subjected to image processing at the control device 9, and various kinds of information related to the endoscope system 1. The display device 7 is implemented by use of a display monitor of, for example, liquid crystal or organic electroluminescence (EL).

One end of the second transmission cable 8 is detachably connected to the display device 7, and the other end of the second transmission cable 8 is detachably connected to the control device 9. The second transmission cable 8 transmits image data that have been subjected to image processing at the control device 9, to the display device 7.

The control device 9 is implemented by use of: a processor that is a processing device having hardware, such as a graphics processing unit (GPU), an FPGA, or a CPU; and a memory that is a transitory storage area used by the processor. According to a program recorded in the memory, the control device 9 integrally controls operation of the light source device 3, the endoscope camera head 5, and the display device 7, via each of the first transmission cable 6, the second transmission cable 8, and the third transmission cable 10. Furthermore, the control device 9 performs various kinds of image processing of image data input via the first transmission cable 6 and outputs the image processed image data to the second transmission cable 8.

One end of the third transmission cable 10 is detachably connected to the light source device 3, and the other end of the third transmission cable 10 is detachably connected to the control device 9. The third transmission cable 10 transmits control data from the control device 9 to the light source device 3.

Functional Configuration of Main Parts of Endoscope System

Figure 2:
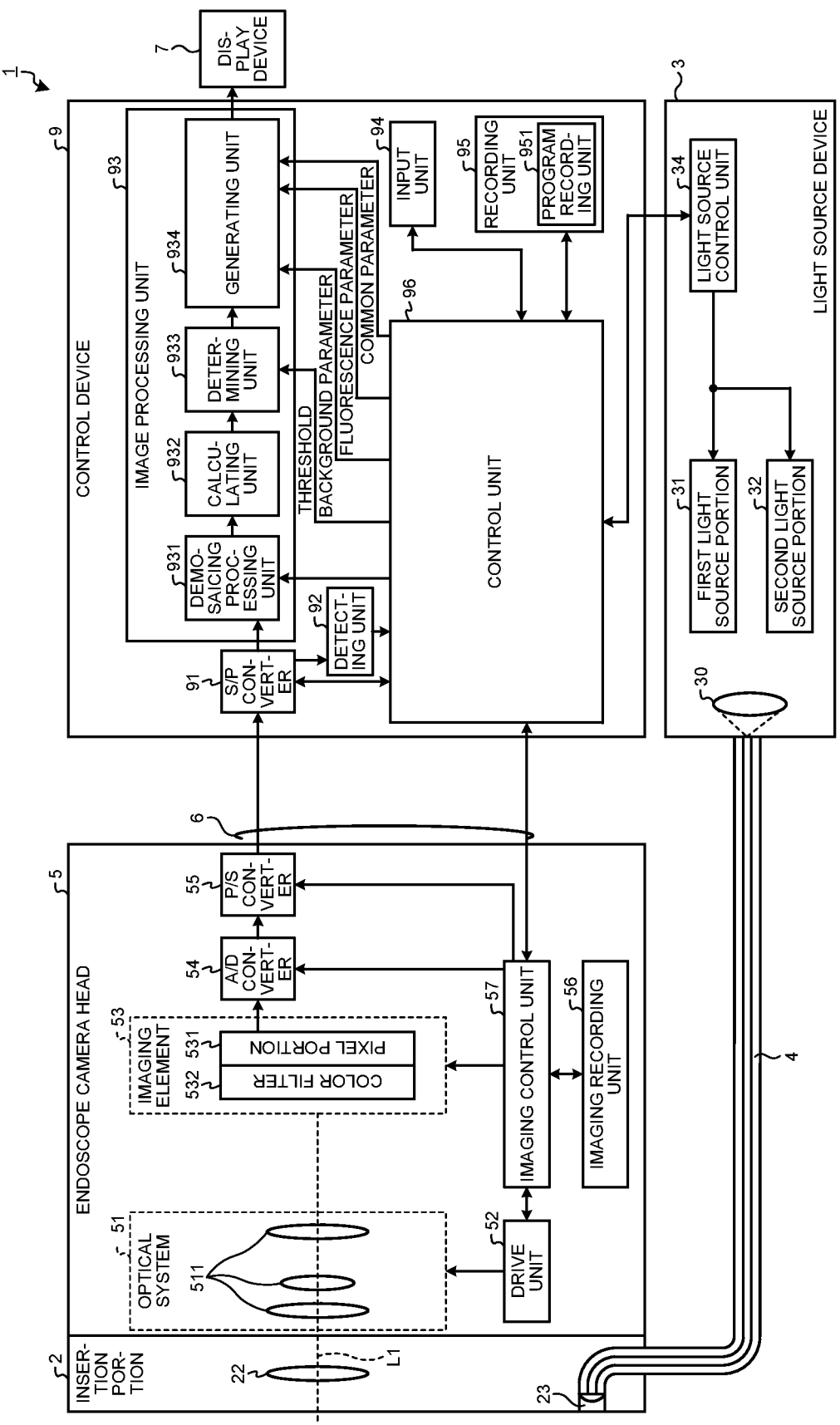
FIG. 2 is a block diagram illustrating a functional configuration of main parts of the endoscope system according to the first embodiment.

A functional configuration of main parts of the endoscope system 1 described above will be described next. FIG. 2 is a block diagram illustrating the functional configuration of the main parts of the endoscope system 1.

Configuration of Insertion Portion

A configuration of the insertion portion 2 will be described first. The insertion portion 2 includes an optical system 22 and an illumination optical system 23.

The optical system 22 condenses light, such as reflected light reflected by a subject, returned light from the subject, excitation light from the subject, and/or light emitted by the subject. The optical system 22 is implemented by use of, for example, one or plural lenses.

The illumination optical system 23 outputs illumination light supplied from the light guide 4, to a subject. The illumination optical system 23 is implemented by use of, for example, one or plural lenses.

Configuration of Light Source Device

A configuration of the light source device 3 will be described next. The light source device 3 includes a condenser lens 30, a first light source portion 31, a second light source portion 32, and a light source control unit 34.

The condenser lens 30 condenses light emitted by each of the first light source portion 31 and the second light source portion 32 and outputs the condensed light to the light guide 4.

Under control by the light source control unit 34, the first light source portion 31 supplies illumination light that is white light (normal light) that is visible light, to the light guide 4 by emitting the white light. The first light source portion 31 is configured by use of, for example, a collimator lens, a white LED lamp, and a driver. The first light source portion 31 may output visible white light by simultaneous emission using a red LED lamp, a green LED lamp, and a blue LED lamp. Of course, the first light source portion 31 may be configured by use of, for example, a halogen lamp or a xenon lamp.

Under control by the light source control unit 34, the second light source portion 32 supplies illumination light that is narrow band light, to the light guide 4 by emitting the narrow band light. The narrow band light includes at least part of a wavelength band of 390 nm to 470 nm. The second light source portion 32 is configured by use of, for example, a collimator lens, a violet LED, and a driver.

The light source control unit 34 is implemented by use of: a processor that is a processing device having hardware, such as an FPGA or a CPU; and a memory that is a transitory storage area used by the processor. On the basis of control data input from the control device 9, the light source control unit 34 controls the emission timing and emission time period of each of the first light source portion 31 and the second light source portion 32.

Figure 3:
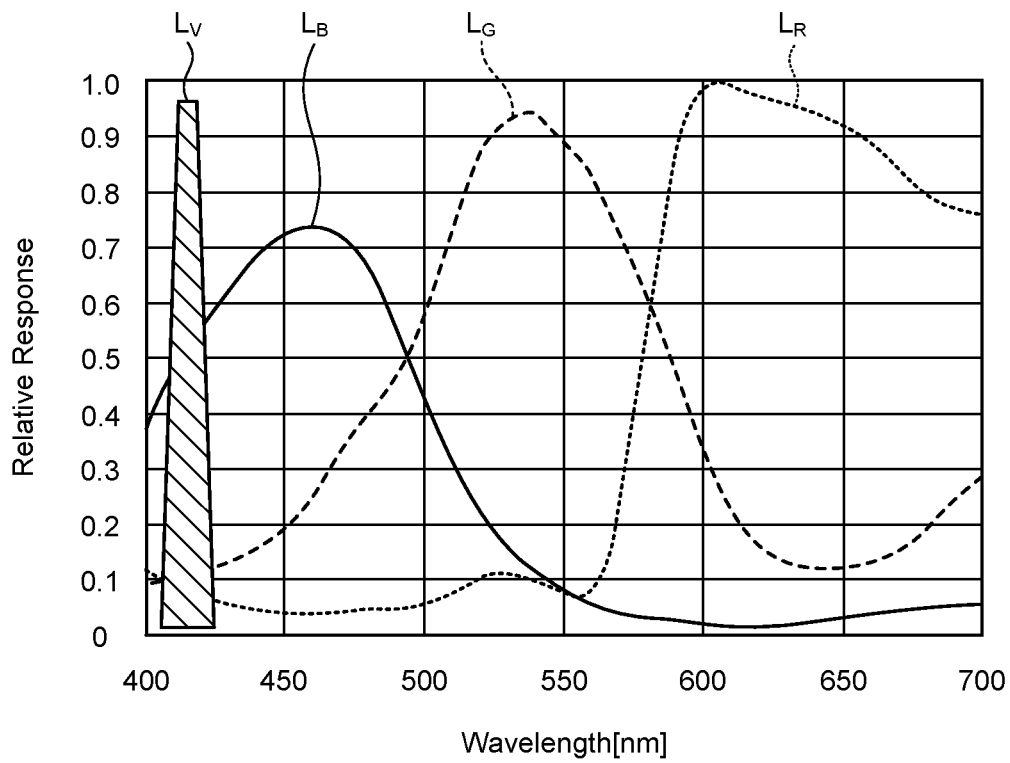
FIG. 3 is a diagram schematically illustrating wavelength characteristics of light emitted by a second light source portion according to the first embodiment.

The following description is on wavelength characteristics of light emitted by the second light source portion 32. FIG. 3 is a diagram schematically illustrating the wavelength characteristics of the light emitted by the second light source portion 32. In FIG. 3, the horizontal axis represents wavelength in nanometers (nm), and the vertical axis represents the wavelength characteristics. A polygonal line $L_V$ in FIG. 3 represents wavelength characteristics of the narrow band light emitted by the second light source portion 32. A curve $L_B$ in FIG. 3 represents a blue wavelength band, a curve $L_G$ represents a green wavelength band, and a curve $L_R$ represents a red wavelength band.

As represented by the polygonal line $L_V$ in FIG. 3, the second light source portion 32 emits narrow band light including at least part of the wavelength band of 390 nm to 470 nm.

Configuration of Endoscope Camera Head

By reference back to FIG. 2, the description of the configuration of the endoscope system 1 will be continued.

A configuration of the endoscope camera head 5 will be described next. The endoscope camera head 5 includes an optical system 51, a drive unit 52, an imaging element 53, an A/D converter 54, a P/S converter 55, an imaging recording unit 56, and an imaging control unit 57.

The optical system 51 forms, on a light receiving surface of the imaging element 53, a subject image condensed by the optical system 22 of the insertion portion 2. The focal length and the focal position of the optical system 51 are able to be changed. The optical system 51 is configured by use of plural lenses 511. In the optical system 51, the plural lenses 511 are moved along an optical axis L1 by the drive unit 52, and the focal distance and focal position are thereby changed.

Under control by the imaging control unit 57, the drive unit 52 moves the plural lenses 511 of the optical system 51 along the optical axis L1. The drive unit 52 is configured by use of: a motor, such as a stepping motor, a DC motor, or a voice coil motor; and a transmission mechanism, such as a gear, that transmits rotation of the motor to the optical system 51.

The imaging element 53 is implemented by use of a charge coupled device (CCD) image sensor or a complementary metal oxide semiconductor (CMOS) image sensor. Under control by the imaging control unit 57, the imaging element 53 receives, via a cut filter 58, a subject image (light rays) formed by the optical system 51, photoelectrically converts the subject image to generate image data (RAW data), and outputs the image data to the A/D converter 54. The imaging element 53 includes a pixel portion 531 and a color filter 532.

Figure 4:
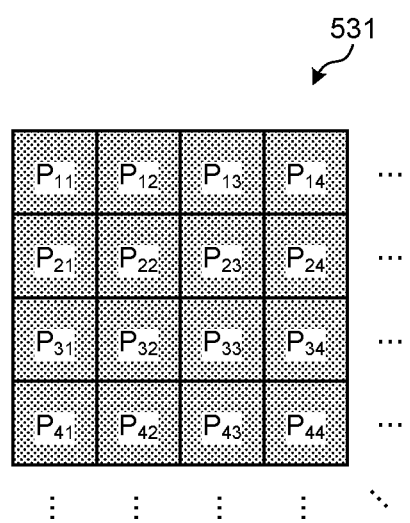
FIG. 4 is a diagram schematically illustrating a configuration of a pixel portion according to the first embodiment.

FIG. 4 is a diagram schematically illustrating a configuration of the pixel portion 531. As illustrated in FIG. 4, the pixel portion 531 has plural pixels $P_{nm}$ (n is an integer equal to or larger than 1 and m is an integer equal to or larger than 1), such as photodiodes that accumulate electric charge corresponding to quantity of light, the plural pixels $P_{nm}$ being arranged in a two-dimensional matrix. Under control by the imaging control unit 57, the pixel portion 531 reads image data that are image signals from some pixels $P_{nm}$ of a read area optionally set as a target to be read from the plural pixels $P_{nm}$ and outputs the image data to the A/D converter 54.

Figure 5:
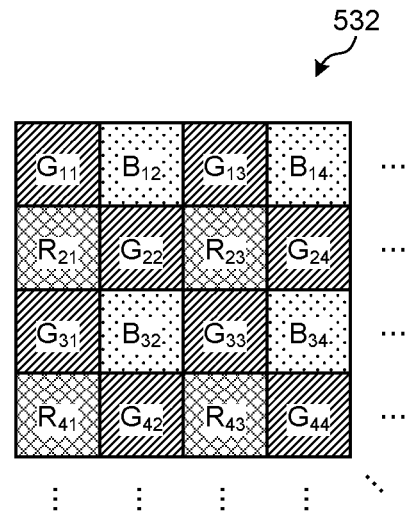
FIG. 5 is a diagram schematically illustrating a configuration of a color filter according to the first embodiment.

FIG. 5 is a diagram schematically illustrating a configuration of the color filter 532. As illustrated in FIG. 5, the color filter 532 has a Bayer arrangement having 2×2 filters as a single unit. The color filter 532 is configured by use of a filter R that transmits therethrough light of the red wavelength band, two filters G that transmit therethrough light of the green wavelength band, and a filter B that transmits therethrough light of the blue wavelength band.

Figure 6:
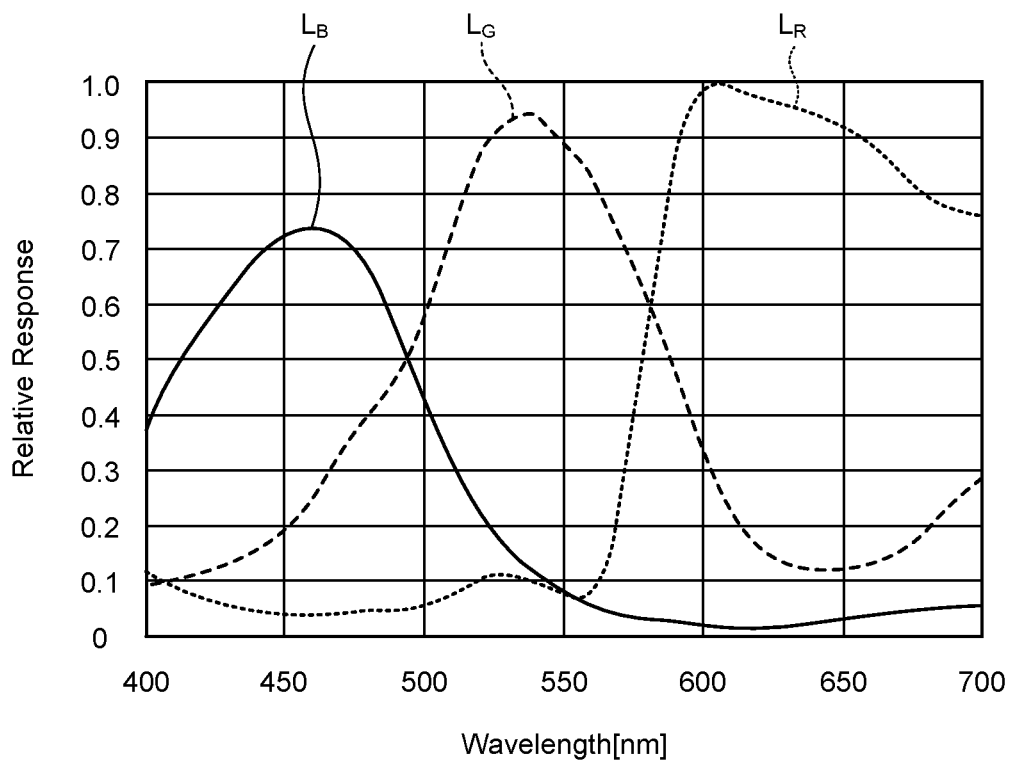
FIG. 6 is a diagram schematically illustrating sensitivity and wavelength bands of filters, according to the first embodiment.

FIG. 6 is a diagram schematically illustrating sensitivity and the wavelength band of each filter. In FIG. 6, the horizontal axis represents wavelength in nanometers (nm) and the vertical axis represents transmission characteristics (sensitivity characteristics). Furthermore, in FIG. 6, a curve $L_B$ represents transmission characteristics of the filter B, a curve $L_G$ represents transmission characteristics of the filter G, and a curve $L_R$ represents the transmission characteristics of the filter R.

As represented by the curve $L_B$ in FIG. 6, the filter B transmits therethrough light of the blue wavelength band. Furthermore, as represented by the curve $L_G$ in FIG. 6, the filter G transmits therethrough light of the green wavelength band. In addition, as represented by the curve $L_R$ in FIG. 6, the filter R transmits therethrough light of the red wavelength band. In the following description, pixels $P_{nm}$ having filters R arranged on light receiving surfaces thereof will be referred to as R pixels, pixels $P_{nm}$ having filters G arranged on light receiving surfaces thereof will be referred to as G pixels, and pixels $P_{nm}$ having filters B arranged on light receiving surfaces thereof will be referred to as B pixels.

Figure 7A:
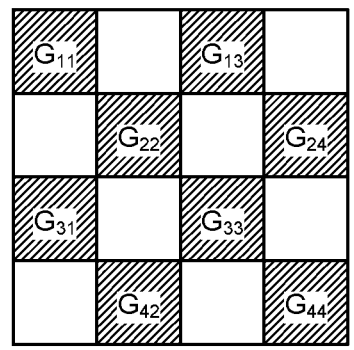
FIG. 7A is a diagram schematically illustrating signal values of G pixels of an imaging element according to the first embodiment.
Figure 7B:
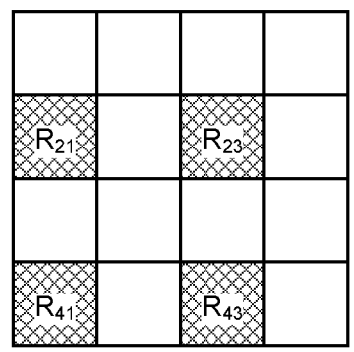
FIG. 7B is a diagram schematically illustrating signal values of R pixels of the imaging element according to the first embodiment.
Figure 7C:
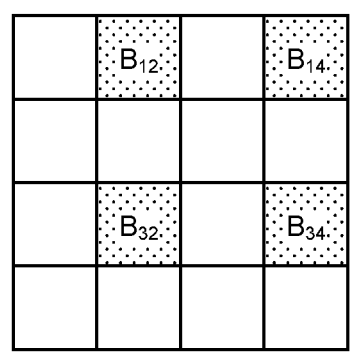
FIG. 7C is a diagram schematically illustrating signal values of B pixels of the imaging element according to the first embodiment.

In a case where a subject image formed by the optical system 51 is received by the imaging element 53 configured as described above, the imaging element 53 generates, as illustrated in FIG. 7A to FIG. 7C, color signals (red component signals, green component signals, and blue component signals) of the R pixels, G pixels, and B pixels respectively.

Under control by the imaging control unit 57, the A/D converter 54 performs A/D conversion processing of analog image data input from the imaging element 53 and outputs the converted image data to the P/S converter 55. The A/D converter 54 is implemented by use of, for example, an A/D conversion circuit.

Under control by the imaging control unit 57, the P/S converter 55 performs parallel/serial conversion of digital image data input from the A/D converter 54, and outputs the image data that have been subjected to the parallel/serial conversion, to the control device 9, via the first transmission cable 6. The P/S converter 55 is implemented by use of, for example, a P/S conversion circuit. In this first embodiment, an E/O converter that converts image data into an optical signal may be provided instead of the P/S converter 55, and the image data may be output through the optical signal to the control device 9, or image data may be transmitted to the control device 9 by wireless communication, such as Wi-Fi (Wireless Fidelity) (registered trademark), for example.

The imaging recording unit 56 records therein various kinds of information related to the endoscope camera head 5 (for example, characteristics of pixel information on the imaging element 53). Furthermore, the imaging recording unit 56 records therein various kinds of setting data and control parameters transmitted from the control device 9 via the first transmission cable 6. The imaging recording unit 56 is configured by use of a nonvolatile memory or a volatile memory.

On the basis of setting data received from the control device 9 via the first transmission cable 6, the imaging control unit 57 controls operation of each of the drive unit 52, the imaging element 53, the A/D converter 54, and the P/S converter 55. The imaging control unit 57 is implemented by use of: a timing generator (TG); a processor that is a processing device having hardware, such as a CPU; and a memory that is a transitory storage area used by the processor.

Configuration of Control Device

A configuration of the control device 9 will be described next.

The control device 9 includes an S/P converter 91, a detecting unit 92, an image processing unit 93, an input unit 94, a recording unit 95, and a control unit 96.

Under control by the control unit 96, the S/P converter 91 performs serial/parallel conversion of image data received from the endoscope camera head 5 via the first transmission cable 6, and outputs the converted image data to the image processing unit 93. In a case where the endoscope camera head 5 outputs the image data as an optical signal, an O/E converter that converts the optical signal into an electric signal may be provided instead of the S/P converter 91. Furthermore, in a case where the endoscope camera head 5 transmits the image data by wireless communication, a communication module capable of receiving a wireless signal may be provided instead of the S/P converter 91.

On the basis of a captured image corresponding to image data input from the S/P converter 91, the detecting unit 92 detects a brightness level from a brightness value of each pixel, and outputs this brightness level to each of the image processing unit 93 and the control unit 96. For example, the brightness level of the captured image detected by the detecting unit 92 is a statistical value of brightness values of pixels, such as a mean value or a median value.

Under control by the control unit 96, the image processing unit 93 performs predetermined image processing of image data in the form of parallel data input from the S/P converter 91 and outputs the processed image data to the display device 7. This predetermined image processing may include any of gain control processing, demosaicing processing, white balance processing, gain adjustment processing, γ correction processing, and format conversion processing. The image processing unit 93 is implemented by use of: a processor that is a processing device having hardware, such as a GPU or an FPGA; and a memory that is a transitory storage area used by the processor. In this first embodiment, the image processing unit 93 functions as a medical image processing device.

The following description is on a detailed configuration of the image processing unit 93. The image processing unit 93 includes at least a demosaicing processing unit 931, a calculating unit 932, a determining unit 933, and a generating unit 934.

The demosaicing processing unit 931 obtains image data generated by imaging at least one of: reflected light from body tissue irradiated with narrow band light shorter in wavelength; and fluorescence from an observation target that emits the fluorescence by irradiation of the body tissue with the narrow band light. On the basis of the image data obtained, the demosaicing processing unit 931 then generates a captured image having color component signals including a red component signal representing a red component, a green component signal representing a green component, and a blue component signal representing a blue component. Specifically, the demosaicing processing unit 931 interpolates pixel values (color component signals) of pixels by well known demosaicing processing.

Under control by the control unit 96, the calculating unit 932 calculates, on the basis of a captured image, an intensity ratio between: a fluorescent component signal that is one of a red component signal, a green component signal, and a blue component signal, the one being highly sensitive to fluorescence; and a reflected light component signal that is another one of the red component signal, the green component signal, and the blue component signal, the other one being highly sensitive to reflected light from body tissue irradiated with narrow band light.

On the basis of the intensity ratio in each pixel of the captured image and calculated by the calculating unit 932, the determining unit 933 determines a fluorescence region and a background region in the captured image. Specifically, under control by the control unit 96 described later, the determining unit 933 determines, on the basis of a threshold set by the control unit 96 and the intensity ratio in each pixel of the captured image and calculated by the calculating unit 932, the fluorescence region and the background region in the captured image.

On the basis of a result of determination by the determining unit 933, the generating unit 934 generates a fluorescence image by performing image processing of color component signals of pixels positioned in the fluorescence region in the captured image and color component signals of pixels positioned in the background region in the captured image, the image processing using parameters different from each other. Specifically, the generating unit 934 performs image processing for a fluorescence parameter for the color component signals of the pixels positioned in the fluorescence region, the image processing being gain adjustment processing where gains for the color component signals of the pixels positioned in the fluorescence region are made larger than gains for the color component signals of the pixels positioned in the background region. In contrast, the generating unit 934 performs image processing for a background parameter for the color component signals of the pixels positioned in the background region, the image processing being gain adjustment processing where gains for the color component signals of the pixels positioned in the background region are made smaller than gains for the color component signals of pixels positioned in the fluorescence region. Furthermore, the generating unit 934 generates the fluorescence image by performing image processing for a fluorescence parameter and a background parameter different from each other respectively for the fluorescence region and the background region, other than the gain adjustment processing. A fluorescence parameter and a background parameter may be for, for example, white balance adjustment processing, contour enhancement processing, contrast enhancement processing, γ correction processing, or hue conversion processing.

The input unit 94 receives input of various operations related to the endoscope system 1 and outputs the received operations to the control unit 96. The input unit 94 is configured by use of a mouse, a foot switch, a keyboard, a button, a switch, and/or a touch panel, for example.

The recording unit 95 is implemented by use of a volatile memory, a nonvolatile memory, a solid state drive (SSD), a hard disk drive (HDD), and/or a recording medium, such as a memory card. The recording unit 95 records therein data including various parameters needed for operation of the endoscope system 1. Furthermore, the recording unit 95 includes a program recording unit 951 that records therein various programs for operation of the endoscope system 1.

The control unit 96 is implemented by use of: a processor that is a processing device having hardware, such as an FPGA or a CPU; and a memory that is a transitory storage area used by the processor. The control unit 96 integrally controls the units included in the endoscope system 1. Furthermore, on the basis of a brightness level detected by the detecting unit 92, the control unit 96 sets a threshold for determination of a fluorescence region and a background region in a captured image by the determining unit 933. In addition, on the basis of an instruction signal input from the input unit 94 and specifying an observation mode that is able to be executed by the endoscope system 1, the control unit 96 sets a fluorescent component signal and a reflected light component signal for an intensity ratio to be calculated by the calculating unit 932.

Processing by Endoscope System

Figure 8:
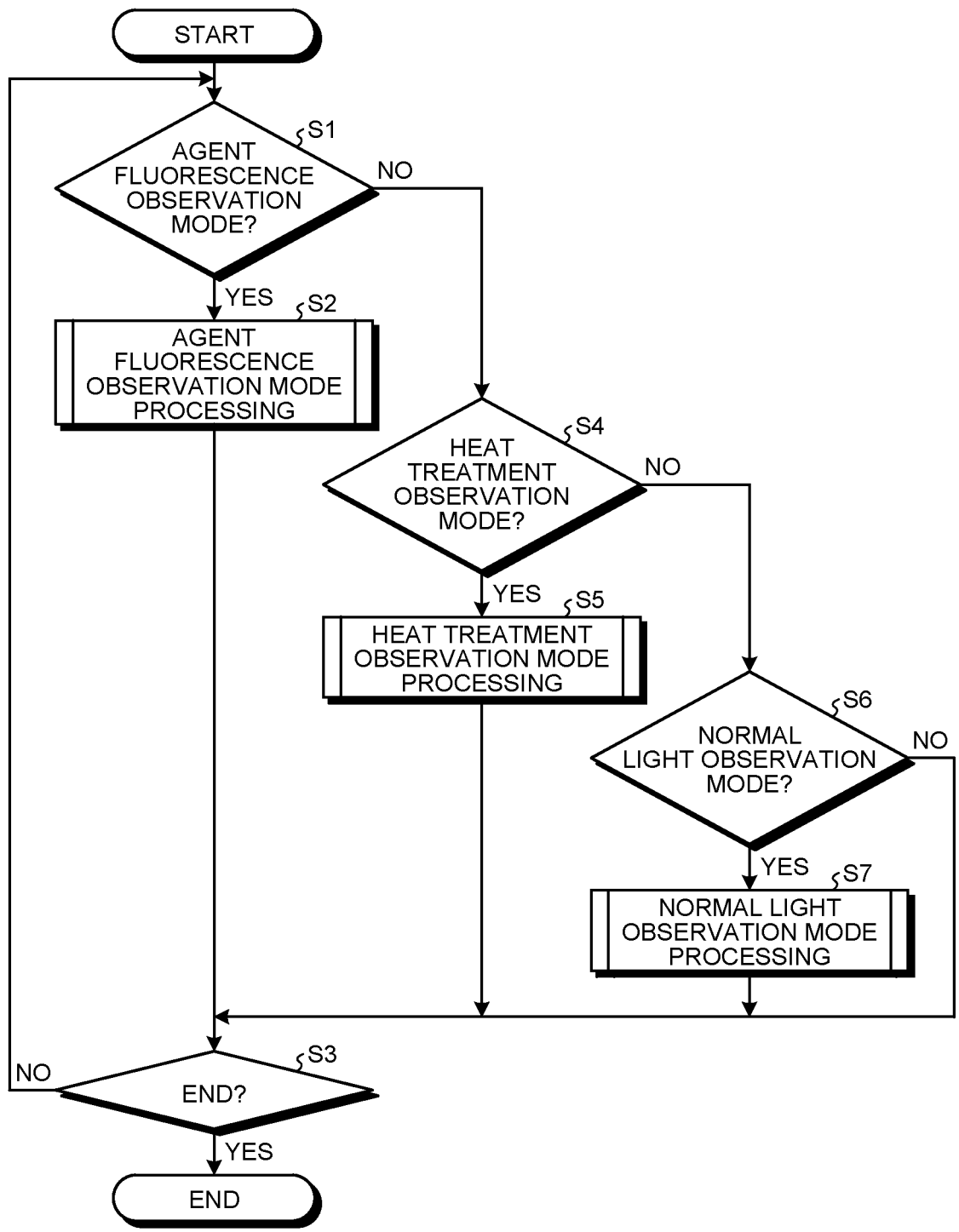
FIG. 8 is a flowchart illustrating an outline of processing executed by the endoscope system according to the first embodiment.

Processing executed by the endoscope system 1 will be described next. FIG. 8 is a flowchart illustrating an outline of the processing executed by the endoscope system 1. The image processing unit 93 performs various kinds of image processing for developing image data, but for simplification, only characteristic image processing in each observation mode will be described hereinafter.

As illustrated in FIG. 8, firstly, the control unit 96 determines, according to a mode signal input from the input unit 94 and indicating an observation mode, whether or not the endoscope system 1 has been set in an agent fluorescence observation mode (Step S1). In a case where the control unit 96 determines that the endoscope system 1 has been set in the agent fluorescence observation mode (Step S1: Yes), the endoscope system 1 proceeds to Step S2 described later. On the contrary, in a case where the control unit 96 determines that the endoscope system 1 has not been set in the agent fluorescence observation mode (Step S1: No), the endoscope system 1 proceeds to Step S4 described later.

At Step S2, the endoscope system 1 executes agent fluorescence observation mode processing. After Step S2, the endoscope system 1 proceeds to Step S3 described later.

Agent Fluorescence Observation Mode Processing

Figure 9:
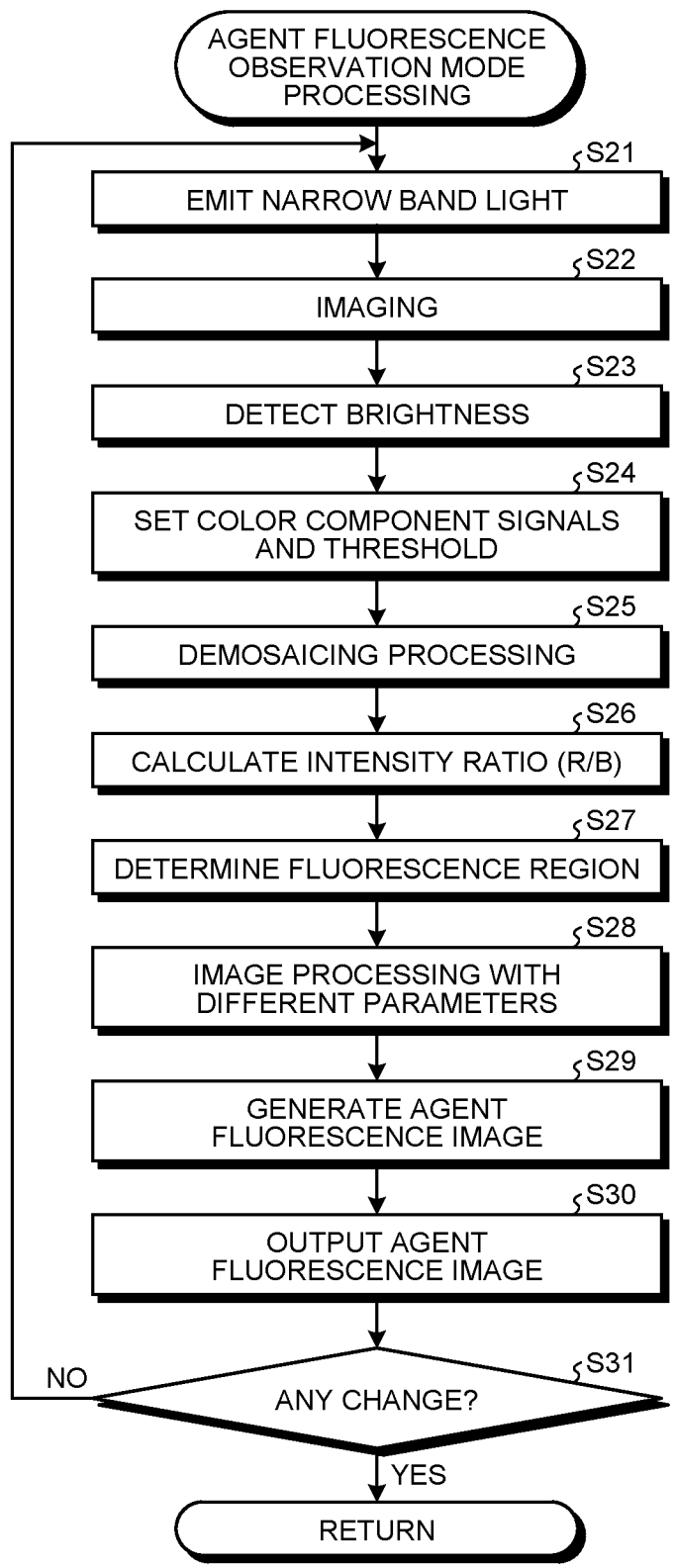
FIG. 9 is a flowchart illustrating an outline of agent fluorescence observation mode processing in FIG. 8.
Figure 10:
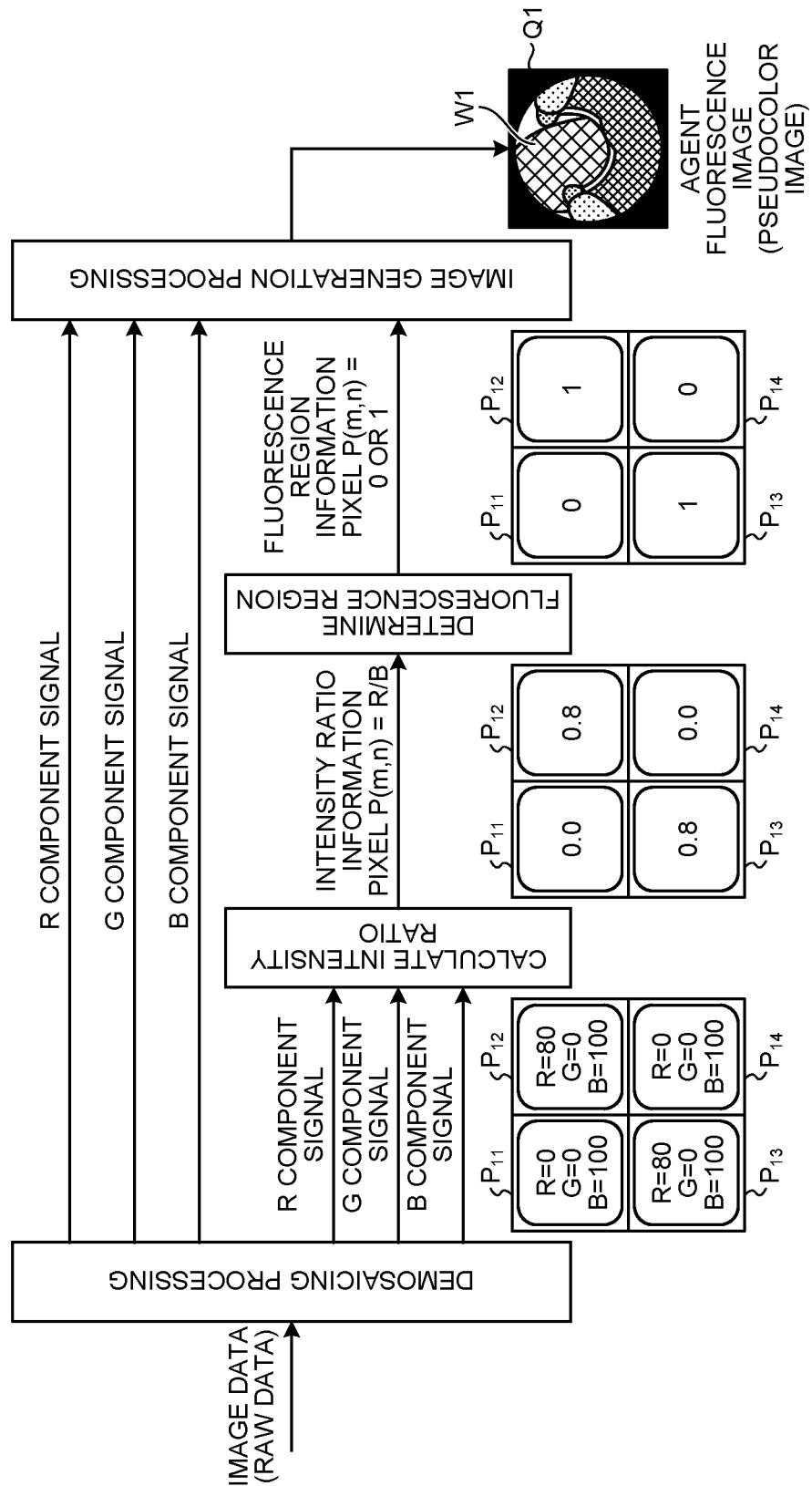
FIG. 10 is a diagram schematically illustrating an outline of image processing in the agent fluorescence observation mode processing by an image processing unit according to the first embodiment.

FIG. 9 is a flowchart illustrating an outline of the agent fluorescence observation mode processing at Step S2 in FIG. 8. FIG. 10 is a diagram schematically illustrating an outline of image processing in the agent fluorescence observation mode processing by the image processing unit 93. A case where PDD observation is performed as agent fluorescence observation will be described with respect to FIG. 9.

Excitation light used in the PDD observation is, for example, blue visible light of a wavelength band of 375 nm to 445 nm (with a central wavelength of 410 nm). An observation target in a subject is subjected to treatment, such as administration of a photosensitive substance, such as 5-aminolevulinic acid (hereinafter, referred to as "5-ALA"). An operating surgeon, such as a medical doctor, may let a subject, such as a patient, take a solution of 5-ALA. The substance, 5-ALA, is a natural amino acid naturally included in living organisms, such as animals and plants. This substance, 5-ALA, is taken into cells after administration into the body, and is formed into protoporphyrin by biosynthesis in mitochondria. This protoporphyrin accumulates excessively in cancer cells. Furthermore, protoporphyrin excessively accumulated in cancer cells are photoactive. Therefore, when excited by excitation light (for example, the blue visible light of the wavelength band of 375 nm to 445 nm), protoporphyrin emits fluorescence (for example, red fluorescence of a wavelength band of 600 nm to 740 nm). The PDD observation is thus observation where photodynamic diagnosis is used. This photodynamic diagnosis is a method of diagnosing cancer by causing cancer cells to emit fluorescence using a photosensitive substance.

As illustrated in FIG. 9, firstly, the control unit 96 controls the light source control unit 34 to cause the second light source portion 32 to emit light and thereby cause narrow band light to be emitted to a subject (Step S21).

Subsequently, by controlling the imaging control unit 57, the control unit 96 causes the imaging element 53 to capture a subject image condensed by the optical system 22 and the optical system 51 (Step S22).

Subsequently, on the basis of a captured image corresponding to image data input via the A/D converter 54, the P/S converter 55, and the S/P converter 91, the detecting unit 92 detects a brightness level from brightness values of pixels (Step S23). In this case, the detecting unit 92 outputs the brightness level to each of the image processing unit 93 and the control unit 96.

Subsequently, on the basis of color component signals for an intensity ratio to be calculated by the calculating unit 932 according to an observation mode set for the endoscope system 1 and the brightness level input from the detecting unit 92, the control unit 96 sets a threshold for determination of pixels of the captured image as those of a fluorescence region and a fluorescence region (Step S24).

Thereafter, the demosaicing processing unit 931 performs well known demosaicing processing of image data (RAW data) input via the A/D converter 54, the P/S converter 55, and the S/P converter 91 (Step S25). Specifically, as illustrated in FIG. 10, the demosaicing processing unit 931 generates a captured image by performing the well known demosaicing processing of the image data and outputs this captured image to the calculating unit 932. In this case, as illustrated in FIG. 10, each pixel includes an R component signal, a G component signal, and a B component signal. For example, a pixel $P_{11}$ includes an R component signal having a value of 0 (R=0), a G component signal having a value of 0 (G=0), and a B component signal having a value of 100 (B=100). Furthermore, a pixel $P_{12}$ includes an R component signal having a value of 80 (R=80), a G component signal having a value of 0 (G=0), and a B component signal having a value of 100 (B=100).

Subsequently, on the basis of the color component signals set by the control unit 96, the calculating unit 932 calculates an intensity ratio in each pixel of the captured image input from the demosaicing processing unit 931 (Step S26). Specifically, as illustrated in FIG. 10, the calculating unit 932 calculates, for each pixel of the captured image, an intensity ratio between a fluorescent component and a reflected light component. The fluorescent component is one of the R component signal, G component signal, and B component signal of the pixel and is high in sensitivity to fluorescence in PDD observation. The reflected light component is another one of the R component signal, G component signal, and B component signal of the pixel and is high in sensitivity to reflected light reflected by body tissue irradiated with the narrow band light. More specifically, as represented by the pixel $P_{11}$ in FIG. 10, in the agent fluorescence observation mode, the calculating unit 932 calculates, as its intensity ratio, a value (R/B=0.0) by dividing the value of the R component signal (R=0) by the value of the B component signal (B=100). Furthermore, as represented by the pixel $P_{12}$ in FIG. 10, the calculating unit 932 calculates, as its intensity ratio, a value (R/B=0.8) by dividing the value of the R component signal (R=80) by the value of the B component signal (B=100).

Thereafter, on the basis of the threshold set by the control unit 96 and the intensity ratio of each pixel calculated by the calculating unit 932, the determining unit 933 determines a fluorescence region (Step S27). Specifically, the determining unit 933 determines, for each pixel of the captured image, whether or not the intensity ratio is equal to or larger than the threshold, and determines any pixel with an intensity ratio equal to or larger than the threshold as that of a fluorescence region (as a fluorescence pixel) and any pixel with an intensity ratio less than the threshold as that of a background region (as a background pixel). More specifically, for the pixel $P_{11}$ illustrated in FIG. 10, the determining unit 933 determines that the pixel $P_{11}$ is of the background region because the intensity ratio is 0.0 and less than the threshold (for example, 0.5), and assigns information (for example, "0") to the pixel $P_{11}$, the information indicating that the pixel $P_{11}$ is of the background region (is a background pixel). Furthermore, for the pixel $P_{12}$ illustrated in FIG. 10, the determining unit 933 determines that the $P_{12}$ is of the fluorescence region (is a fluorescence pixel) because the intensity ratio is 0.8 and equal to or larger than the threshold, and assigns information (for example, "1") to the pixel $P_{12}$, the information indicating that the pixel $P_{12}$ is of the fluorescence region (is a fluorescence pixel).

Subsequently, on the basis of image processing parameters set by the control unit 96 according to the type of the endoscope camera head 5 and a result of determination by the determining unit 933, the generating unit 934 performs image processing of each pixel of the captured image input from the demosaicing processing unit 931, the image processing using different parameters (Step S28). Specifically, the generating unit 934 performs image processing for a background parameter to decrease gains for signal values of pixels determined to be of the background region by the determining unit 933. In contrast, the determining unit 933 performs image processing for a fluorescence parameter to increase gains for signal values of pixels determined to be of the fluorescence region by the determining unit 933. Pixel values of the pixels positioned in the fluorescence region are thereby increased, pixels values of the pixels positioned in the background region are thereby decreased, and the fluorescence region is thus able to be enhanced.

Thereafter, the generating unit 934 performs, for each pixel of the captured image that has been subjected to the image processing for the parameters different from each other, for example, γ correction processing, color tone converting processing, white balance processing, and format conversion processing, to generate an agent fluorescence image Q1 (a pseudocolor image) (Step S29).

Subsequently, the generating unit 934 outputs the agent fluorescence image Q1 to the display device 7 (Step S30). An operating surgeon, such as a medical doctor, is thereby able to observe the agent fluorescence image Q1 having the fluorescence region enhanced in relation to the background region.

The control unit 96 determines whether or not a switching signal to change the observation mode of the endoscope system 1 has been input from the input unit 94 (Step S31). In a case where the control unit 96 determines that the switching signal to change the observation mode of the endoscope system 1 has been input from the input unit 94 (Step S31: Yes), the endoscope system 1 returns to the main routine in FIG. 8. On the contrary, in a case where the control unit 96 determines that the switching signal to change the observation mode of the endoscope system 1 has not been input from the input unit 94 (Step S31: No), the endoscope system 1 returns to Step S21 described above.

By reference back to FIG. 8, description of the processing from Step S3 will be continued.

At Step S3, the control unit 96 determines whether or not an instruction signal to instruct the system to end the observation of the subject has been input from the input unit 94. In a case where the control unit 96 determines that the instruction signal to instruct the system to end the observation of the subject has been input from the input unit 94 (Step S3: Yes), the endoscope system 1 ends the processing. On the contrary, in a case where the control unit 96 determines that the instruction signal to instruct the system to end the observation of the subject has not been input from the input unit 94 (Step S3: No), the endoscope system 1 returns to Step S1 described above.

At Step S4, according to a mode signal input from the input unit 94 and indicating an observation mode, the control unit 96 determines whether or not the endoscope system 1 has been set in a heat treatment observation mode. In a case where the control unit 96 determines that the endoscope system 1 has been set in the heat treatment observation mode (Step S4: Yes), the endoscope system 1 proceeds to Step S5 described later. On the contrary, in a case where the control unit 96 determines that the endoscope system 1 has not been set in the heat treatment observation mode (Step S4: No), the endoscope system 1 proceeds to Step S6 described later.

Heat Treatment Observation Mode Processing

Figure 11:
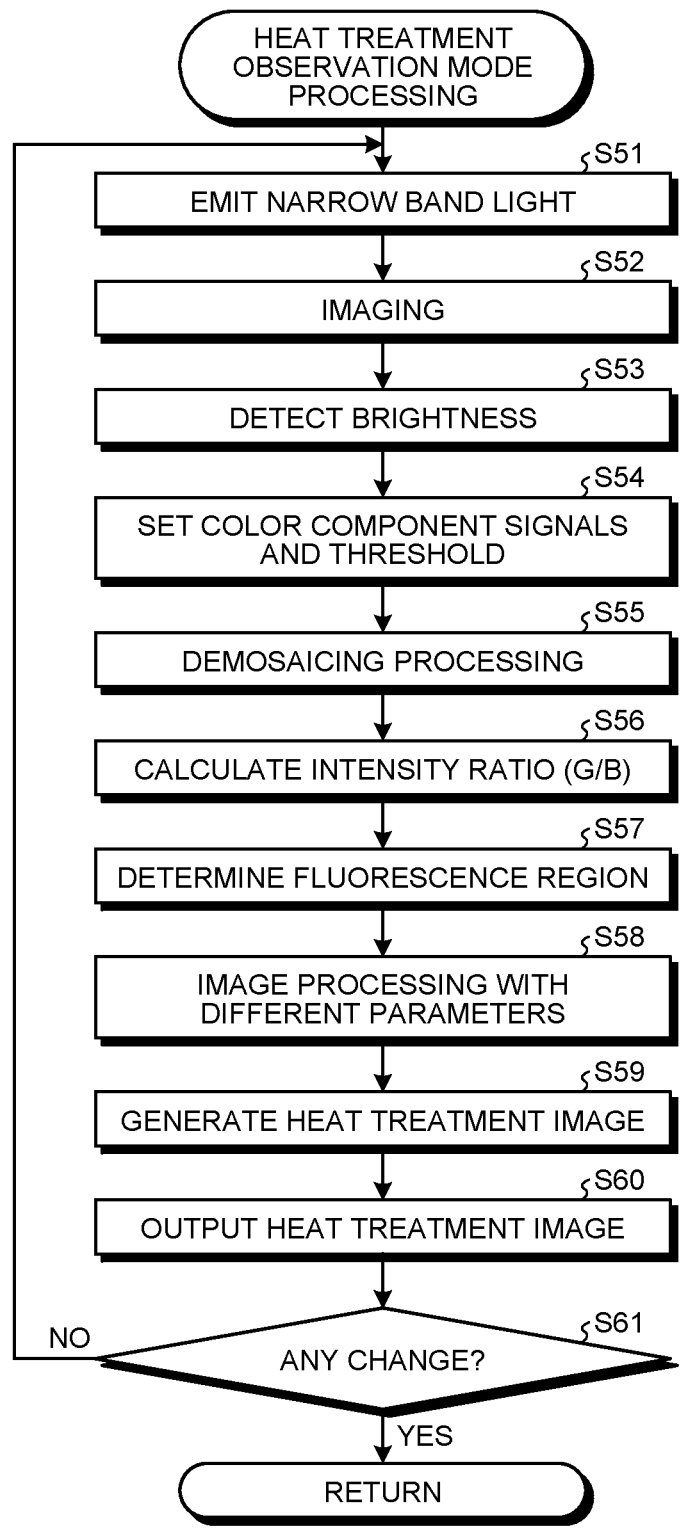
FIG. 11 is a flowchart illustrating an outline of heat treatment observation mode processing in FIG. 8.
Figure 12:
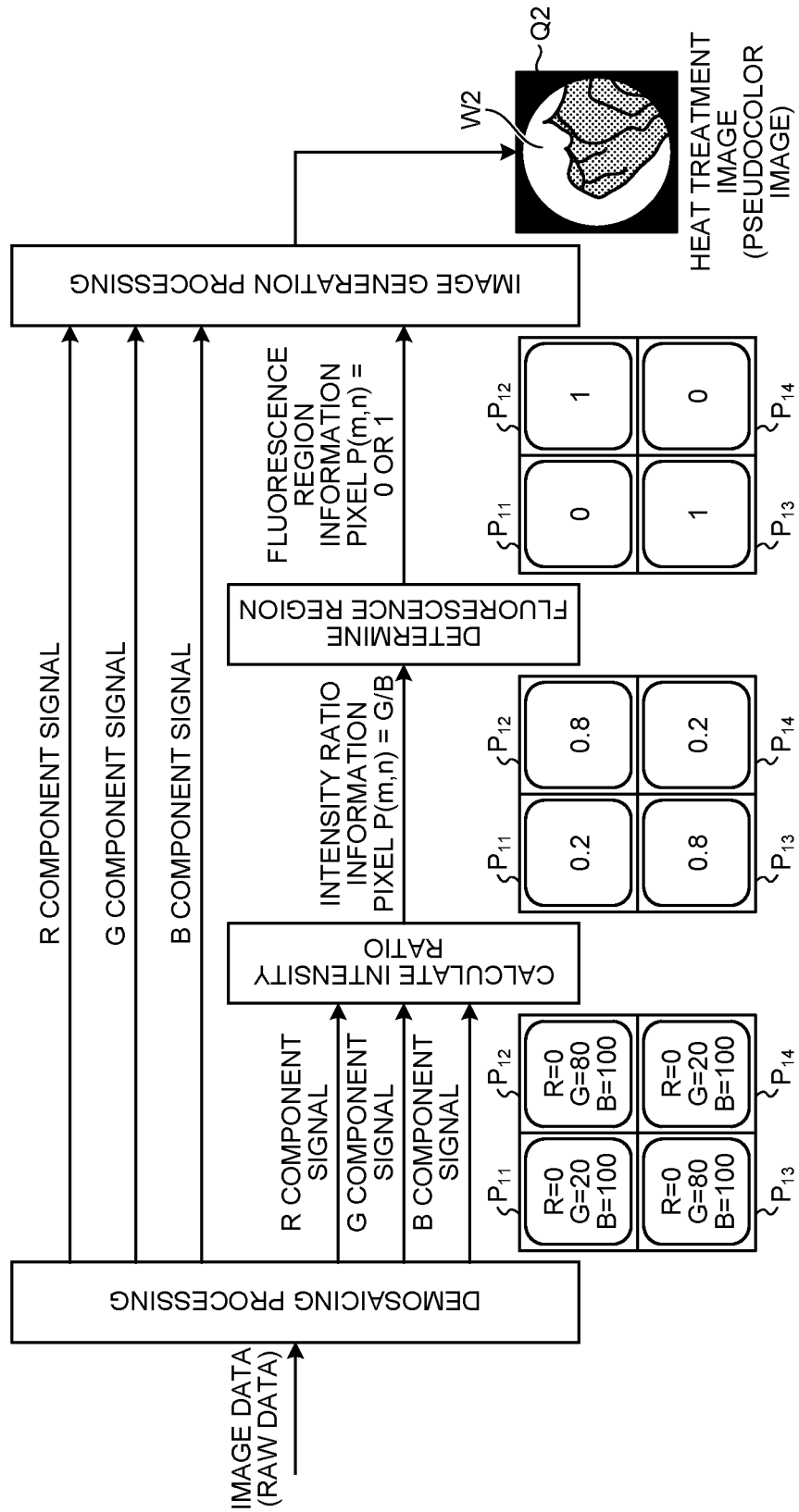
FIG. 12 is a diagram schematically illustrating an outline of image processing in the heat treatment observation mode processing by the image processing unit according to the first embodiment.

FIG. 11 is a flowchart illustrating an outline of heat treatment observation mode processing at Step S5 in FIG. 8 described above. FIG. 12 is a diagram schematically illustrating an outline of image processing in the heat treatment observation mode processing by the image processing unit 93.

In recent years, minimally invasive treatments using, for example, endoscopes and laparoscopes have been widely adopted in the medical field. For example, widely adopted ones of the minimally invasive treatments using endoscopes and laparoscopes include endoscopic submucosal dissection (ESD), laparoscopy and endoscopy cooperative surgery (LECS), and non-exposed endoscopic wall-inversion surgery (NEWS).

In these minimally invasive treatments, for example, an operating surgeon, such as a medical doctor, performs pretreatment that is heat treatment or marking treatment by heat treatment, of body tissue, by use of a treatment tool, such as an energy device that may be, for example, a high frequency knife or an electrosurgical knife, for marking of a region to be operated. Furthermore, for the actual treatment, the operating surgeon also performs treatment, such as excision and coagulation of the body tissue of the subject by using the energy device, for example.

In reality, the extent of the heat treatment applied to the body tissue by the energy device is checked by the operating surgeon on the basis of, for example, the operating surgeon's visual inspection, sense of touch, and/or guess. Therefore, in a conventional treatment using an energy device, for example, it is difficult for an operating surgeon to check in real time the degree of heat treatment to be applied during the operation in surgery and this check requires great skill and experience. Accordingly, there is a demand from operating surgeons for a technology that enables visualization of a cauterization state of a heat-treated region in heat treatment of body tissue conducted by use of an energy device.

A glycation reaction (the Maillard reaction) occurs when an amino acid and a reducing sugar are heated. End products produced as a result of this Maillard reaction are generally called advanced glycation end products (AGEs). AGEs are known to include a substance having fluorescence.

That is, when body tissue is heat-treated by an energy device, AGEs are produced by the Maillard reaction caused by heating of amino acids and reducing sugars in the body tissue. Fluorescence observation of the AGEs produced by this heating enables visualization of states of the heat treatment. In addition, AGEs are known to emit fluorescence that is more intense than that by autofluorescent substances present in body tissue by nature.

That is, the heat treatment observation mode corresponds to an observation method of visualizing a heat-treated region subjected to heat treatment by utilizing fluorescence of AGEs produced in body tissue by heat treatment by means of, for example, an energy device. Accordingly, in the heat treatment observation mode, blue light near a wavelength of 415 nm for exciting the AGEs is emitted from the light source device 3 to the body tissue. In the heat treatment observation mode, a heat treatment image (a fluorescence image) having, captured therein, fluorescence (for example, green light having wavelengths of 490 nm to 625 nm) generated by the AGEs is thereby able to be observed.

As illustrated in FIG. 11, firstly, the control unit 96 causes the second light source portion 32 to emit light by controlling the light source control unit 34 and thereby causes narrow band light to be emitted to a subject (Step S51).

Subsequently, by controlling the imaging control unit 57, the control unit 96 causes the imaging element 53 to capture a subject image condensed by the optical system 22 and the optical system 51 (Step S52).

Subsequently, on the basis of a captured image corresponding to image data input via the A/D converter 54, the P/S converter 55, and the S/P converter 91, the detecting unit 92 detects a brightness level from brightness values of pixels (Step S53). In this case, the detecting unit 92 outputs the brightness level to each of the image processing unit 93 and the control unit 96.

Subsequently, on the basis of the brightness level input from the detecting unit 92, the control unit 96 sets a threshold for determining pixels of a captured image as those of a fluorescence region and a background region (Step S54).

Thereafter, the demosaicing processing unit 931 performs well known demosaicing processing of image data (RAW data) input via the A/D converter 54, the P/S converter 55, and the S/P converter 91 (Step S55). Specifically, as illustrated in FIG. 12, the demosaicing processing unit 931 generates a captured image by performing the well known demosaicing processing of the image data and outputs this captured image to the calculating unit 932. In this case, as illustrated in FIG. 12, each pixel includes an R component signal, a G component signal, and a B component signal. For example, a pixel $P_{11}$ includes an R component signal having a value of 0 (R=0), a G component signal having a value of 20 (G=20), and a B component signal having a value of 100 (B=100). Furthermore, a pixel $P_{12}$ includes an R component signal having a value of 0 (R=0), a G component signal having a value of 80 (G=80), and a B component signal having a value of 100 (B=100).

Subsequently, on the basis of color component signals set by the control unit 96, the calculating unit 932 calculates an intensity ratio in each pixel of the captured image input from the demosaicing processing unit 931 (Step S56). Specifically, as illustrated in FIG. 12, the calculating unit 932 calculates, for each pixel of the captured image, an intensity ratio between a fluorescent component and a reflected light component. The fluorescent component is one of the R component signal, G component signal, and B component signal of the pixel and is high in sensitivity to fluorescence in heat treatment observation. The reflected light component is another one of the R component signal, G component signal, and B component signal of the pixel and is high in sensitivity to reflected light reflected by body tissue irradiated with narrow band light. More specifically, as represented by the pixel $P_{11}$ in FIG. 12, in the heat treatment observation mode, the calculating unit 932 calculates, as the intensity ratio, a value (G/B=0.2) by dividing the value of the G component signal (G=20) by the value of the B component signal (B=100). Furthermore, as represented by the pixel $P_{12}$ in FIG. 12, the calculating unit 932 calculates, as the intensity ratio, a value (G/B=0.8) by dividing the value of the G component signal (G=80) by the value of the B component signal (B=100).

Thereafter, on the basis of the threshold set by the control unit 96 and the intensity ratio of each pixel calculated by the calculating unit 932, the determining unit 933 determines a fluorescence region (Step S57). Specifically, the determining unit 933 determines, for each pixel of the captured image, whether or not the intensity ratio is equal to or larger than the threshold, and determines any pixel with an intensity ratio equal to or larger than the threshold as that of the fluorescence region (a fluorescence pixel) and any pixel with an intensity ratio less than the threshold as that of a background region (a background pixel). More specifically, for the pixel $P_{11}$ illustrated in FIG. 12, the determining unit 933 determines that the pixel $P_{11}$ is of the background region because the intensity ratio is 0.2 and less than the threshold (for example, 0.5), and assigns information (for example, "0") to the pixel $P_{11}$, the information indicating that the pixel $P_{11}$ is of the background region (is a background pixel). Furthermore, for the pixel $P_{12}$ illustrated in FIG. 12, the determining unit 933 determines that the pixel $P_{12}$ is of the fluorescence region (is a fluorescence pixel) because the intensity ratio is 0.8 and equal to or larger than the threshold, and assigns information (for example, "1") to the pixel $P_{12}$, the information indicating that the pixel $P_{12}$ is of the fluorescence region (is a fluorescence pixel).

Subsequently, on the basis of image processing parameters set by the control unit 96 according to the type of the endoscope camera head 5 and a result of determination by the determining unit 933, the generating unit 934 performs image processing of each pixel of the captured image input from the demosaicing processing unit 931, the image processing using parameters different from each other (Step S58). Specifically, the generating unit 934 performs first image processing for a background parameter to reduce gains for signal values of pixels determined to be of the background region by the determining unit 933. In contrast, the determining unit 933 performs the first image processing for a fluorescence parameter to increase gains for signal values of pixels determined to be of the fluorescence region by the determining unit 933. Pixel values of the pixels positioned in the fluorescence region are thereby increased, pixels values of the pixels positioned in the background region are thereby decreased, and the fluorescence region is thus able to be enhanced.

Thereafter, the generating unit 934 performs, for each pixel of the captured image that has been subjected to the image processing for the parameters different from each other, for example, γ correction processing, color tone conversion processing, white balance processing, and format conversion processing, to generate a heat treatment image Q2 (a pseudocolor image) (Step S59).

Subsequently, the generating unit 934 outputs the heat treatment image Q2 to the display device 7 (Step S60). An operating surgeon, such as a medical doctor, is thereby able to observe the heat treatment image Q2 having the heat treated region enhanced in relation to the background region.

The control unit 96 determines whether or not a switching signal to change the observation mode of the endoscope system 1 has been input from the input unit 94 (Step S61). In a case where the control unit 96 determines that the switching signal to change the observation mode of the endoscope system 1 has been input from the input unit 94 (Step S61: Yes), the endoscope system 1 returns to the main routine in FIG. 8. On the contrary, in a case where the control unit 96 determines that the switching signal to change the observation mode of the endoscope system 1 has not been input from the input unit 94 (Step S61: No), the endoscope system 1 returns to Step S51 described above.

By reference back to FIG. 8, description of the processing from Step S6 will be continued.

At Step S6, according to a mode signal input from the input unit 94 and indicating an observation mode, the control unit 96 determines whether or not the endoscope system 1 has been set in a normal light observation mode. In a case where the control unit 96 determines that the endoscope system 1 has been set in the normal light observation mode (Step S6: Yes), the endoscope system 1 proceeds to Step S7 described later. On the contrary, in a case where the control unit 96 determines that the endoscope system 1 has not been set in the normal light observation mode (Step S6: No), the endoscope system 1 proceeds to Step S3.

At Step S7, the endoscope system 1 executes normal light observation mode processing. After Step S7, the endoscope system 1 proceeds to Step S3.

Normal Light Observation Mode Processing

Figure 13:
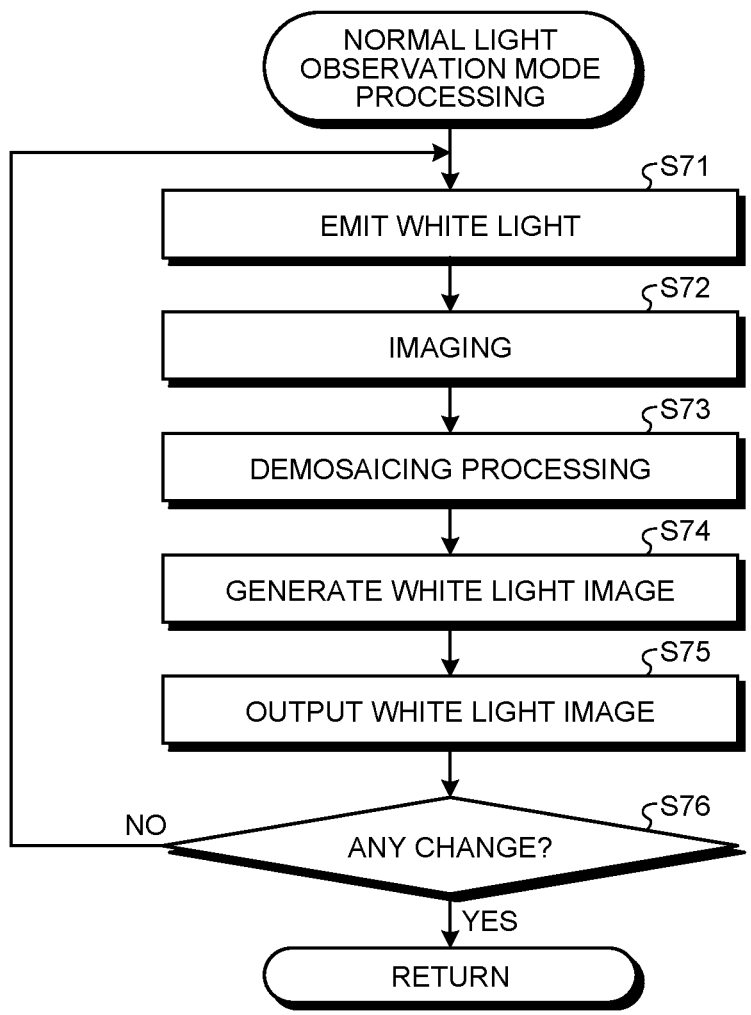
FIG. 13 is a flowchart illustrating an outline of normal light observation mode processing in FIG. 8.
Figure 18:
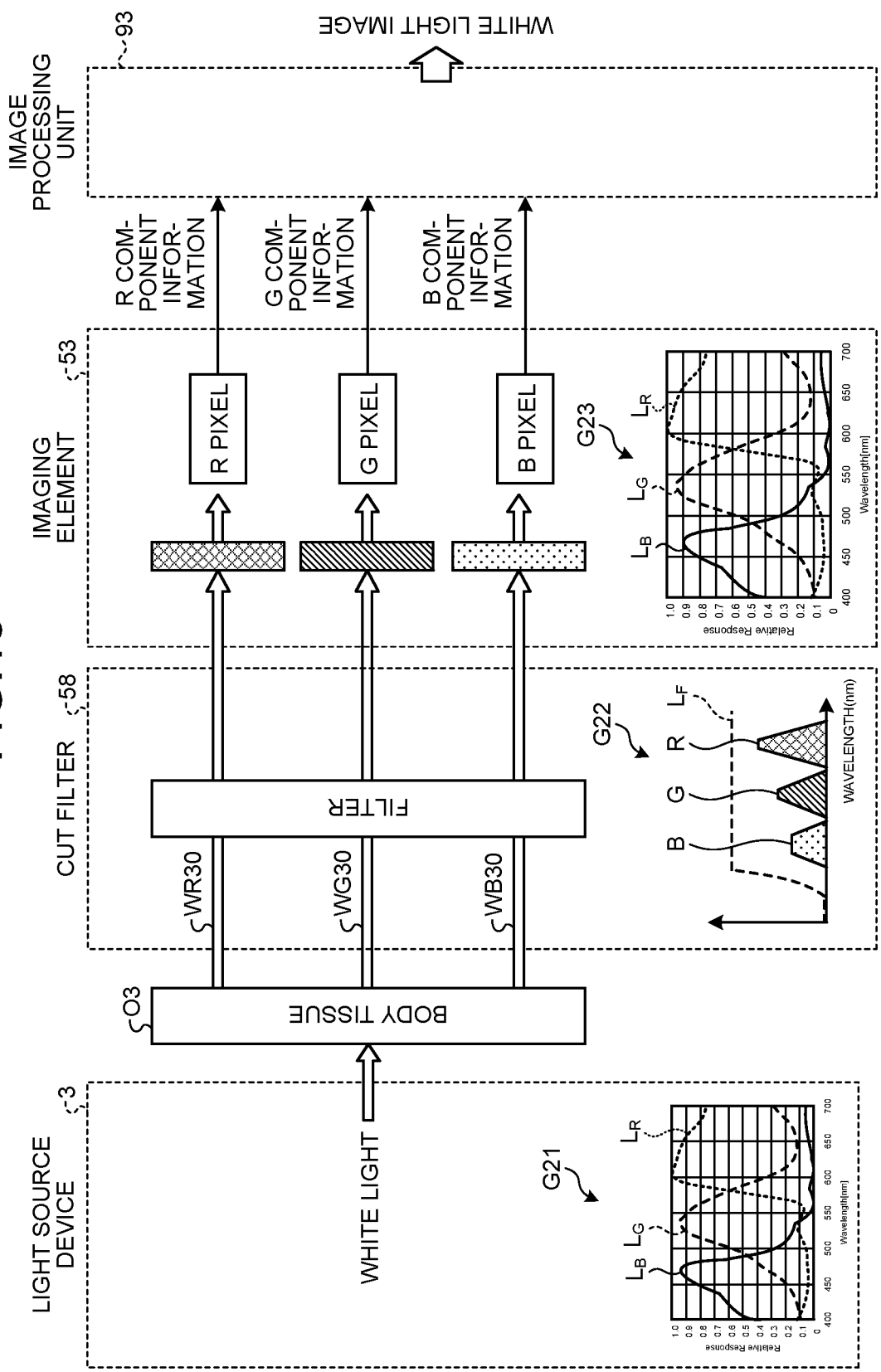
FIG. 18 is a diagram schematically illustrating principles of observation in a normal light observation mode according to the second embodiment.

FIG. 13 is a flowchart illustrating an outline of the normal light observation mode processing at Step S7 in FIG. 18 described above.

As illustrated in FIG. 13, firstly, the control unit 96 causes the first light source portion 31 to emit light by controlling the light source control unit 34 and thereby causes white light to be emitted to a subject (Step S71).

Subsequently, by controlling the imaging control unit 57, the control unit 96 causes the imaging element 53 to capture a subject image condensed by the optical system 22 and the optical system 51 (Step S72).

Thereafter, the control unit 96 causes the demosaicing processing unit 931 to execute demosaicing processing of image data input via the A/D converter 54, the P/S converter 55, and the S/P converter 91 (Step S73).

Subsequently, the generating unit 934 generates a white light image by performing second image processing, such as γ correction processing, color tone conversion processing, white balance processing, and format conversion processing, of the captured image that has been subjected to the demosaicing processing by the demosaicing processing unit 931 (Step S74), and outputs this white light image to the display device 7 (Step S75).

Subsequently, the control unit 96 determines whether or not a switching signal to change the observation mode of the endoscope system 1 has been input from the input unit 94 (Step S76). In a case where the control unit 96 determines that the switching signal to change the observation mode of the endoscope system 1 has been input from the input unit 94 (Step S76: Yes), the endoscope system 1 returns to the main routine in FIG. 8. On the contrary, in a case where the control unit 96 determines that the switching signal to change the observation mode of the endoscope system 1 has not been input from the input unit 94 (Step S76: No), the endoscope system 1 returns to Step S71 described above.

The first embodiment described above enables visibility of fluorescence to be improved because: the calculating unit 932 calculates, for each pixel of a captured image, an intensity ratio between a fluorescent component signal high in sensitivity to fluorescence and reflected light component signal high in sensitivity to reflected light; on the basis of the intensity ratios of the pixels calculated by the calculating unit 932, the determining unit 933 determines a fluorescence region and a background region in the captured image; and the generating unit 934 generates a heat treatment image or an agent fluorescence image by performing image processing with parameters different from each other for color component signals of pixels positioned in the fluorescence region determined by the determining unit 933 and color component signals of pixels positioned in the background region determined by the determining unit 933.

Furthermore, the first embodiment enables visibility of fluorescence to be improved because the generating unit 934 generates the heat treatment image or the agent fluorescence image by performing the image processing that is gain adjustment processing where gains for the color component signals of the pixels positioned in the fluorescence region are made larger than gains for the color component signals of the pixels positioned in the background region.

Furthermore, the first embodiment enables the determining unit 933 to make a determination by discriminating between noise included in the captured image and emission of fluorescence because the control unit 96 sets a threshold on the basis of a result of detection by the detecting unit 92.

Furthermore, the first embodiment enables cost reduction and reduction in size and weight of the endoscope camera head 5 and streamlined control processing by the control device 9 because the endoscope camera head 5 is formed of just the single imaging element 53.

Second Embodiment

A second embodiment will be described next. An endoscope system according to the second embodiment has a configuration different from that of the above described endoscope system 1 according to the first embodiment. Specifically, the endoscope system according to the second embodiment further includes a cut filter that is an optical element that shields reflected light and returned light resulting from reflection of narrow band light by body tissue, the narrow band light serving as excitation light. The configuration of the endoscope system according to the second embodiment will thus be described hereinafter. The same reference signs will be assigned to components that are the same as those of the above described endoscope system 1 according to the first embodiment, and detailed description of these components will thus be omitted.

Functional Configuration of Main Parts of Endoscope System

Figure 14:
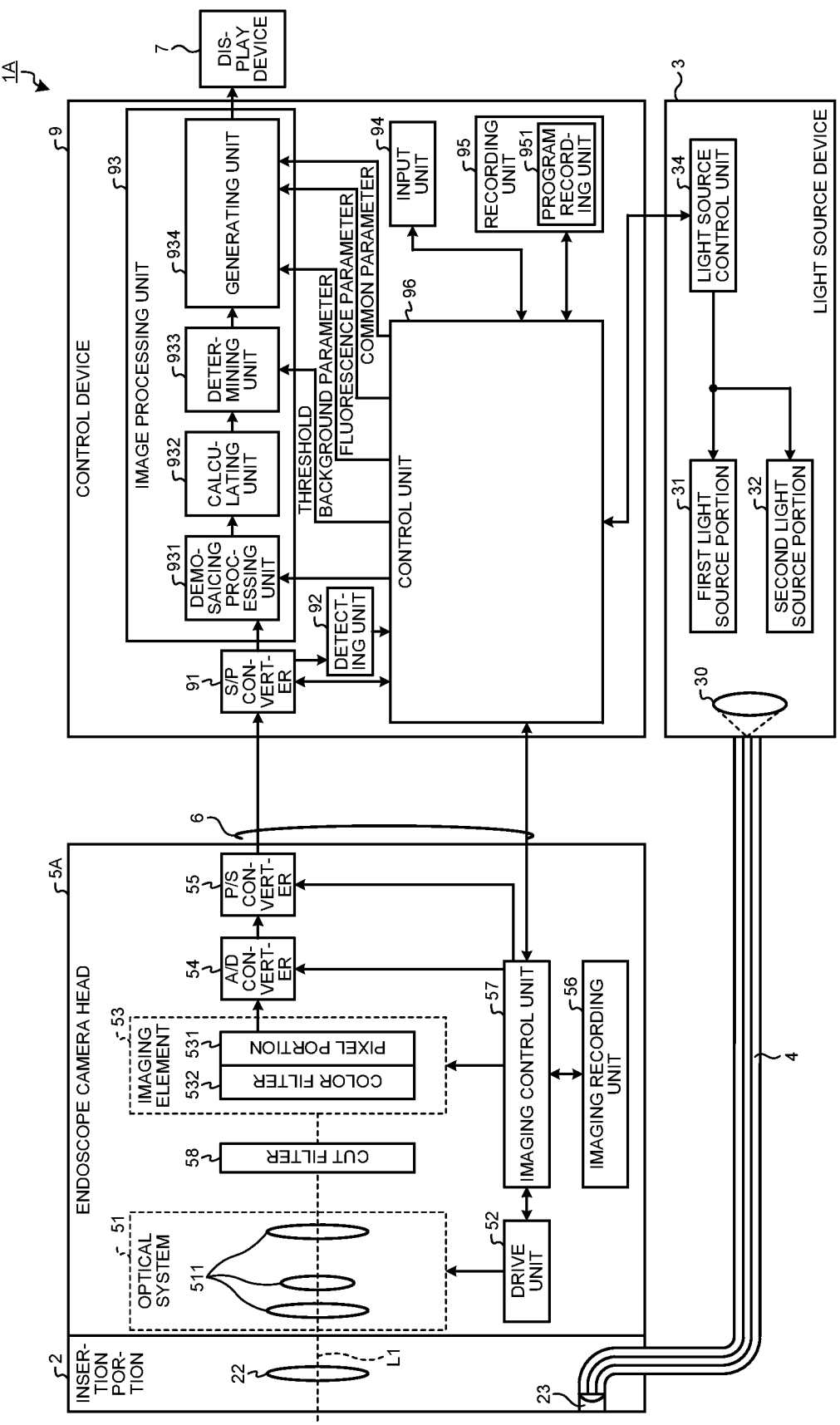
FIG. 14 is a block diagram illustrating a functional configuration of main parts of an endoscope system according to a second embodiment.

FIG. 14 is a block diagram illustrating a functional configuration of main parts of the endoscope system. An endoscope system 1A illustrated in FIG. 14 includes an endoscope camera head 5A, instead of the above described endoscope camera head 5 according to the first embodiment.

Configuration of Endoscope Camera Head

The endoscope camera head 5A further includes a cut filter 58, in addition to the above described configuration of the endoscope camera head 5 according to the first embodiment.

The cut filter 58 is arranged on an optical path of the optical system 51 and the imaging element 53. The cut filter 58 shields most of light of a short wavelength band including a wavelength band of narrow band light and transmits therethrough light of a wavelength band longer than this short wavelength band of the light that is mostly shielded.

Figure 15A:
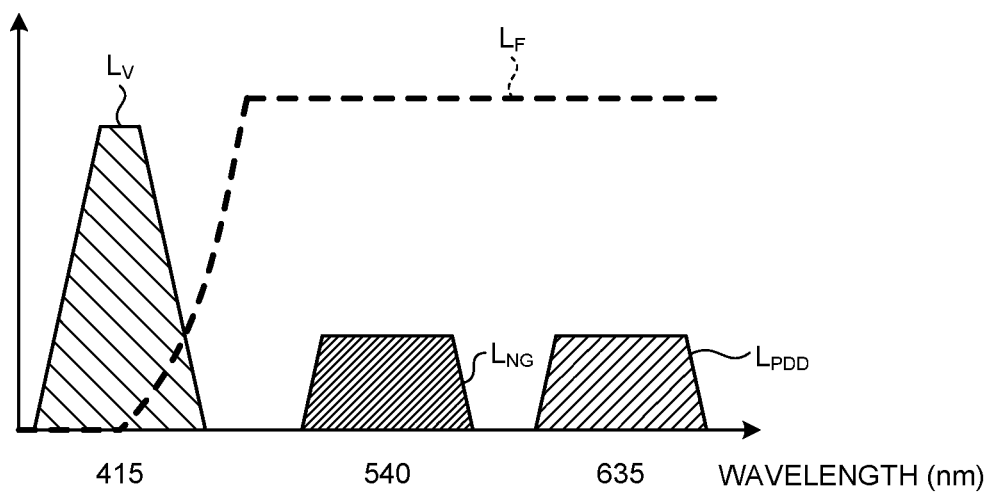
FIG. 15A is a diagram schematically illustrating transmission characteristics of a cut filter according to the second embodiment.

FIG. 15A is a diagram schematically illustrating transmission characteristics of the cut filter 58. In FIG. 15A, the horizontal axis represents wavelength in nanometers (nm) and the vertical axis represents transmission characteristics. Furthermore, in FIG. 15A, a polygonal line $L_F$ represents the transmission characteristics of the cut filter 58, a polygonal line $L_V$ represents wavelength characteristics of the narrow band light, a polygonal line $L_{NG}$ represents wavelength characteristics of fluorescence of AGEs, and a polygonal line $Lp_{PDD}$ represents wavelength characteristics of fluorescence of 5-ALA.

As illustrated in FIG. 15A, the cut filter 58 shields most of the light of the short wavelength band and transmits therethrough light of the wavelength band longer than this short wavelength band of the light that is mostly shielded. Specifically, the cut filter 58 shields most of light of a shorter wavelength band less than any wavelength of 430 nm to 470 nm including the wavelength band of the narrow band light and transmits therethrough light of the wavelength band longer than this shorter wavelength band of the light that is mostly shielded. For example, as represented by the polygonal line $L_{NG}$ and the polygonal line $L_{PDD}$, the cut filter 58 transmits therethrough the fluorescence of AGEs produced by heat treatment and the fluorescence of 5-ALA.

Figure 15B:
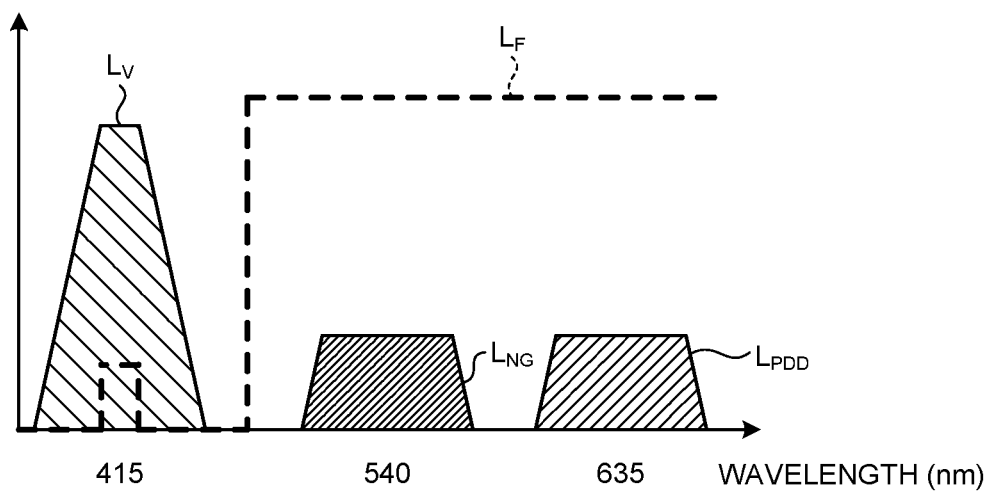
FIG. 15B is a diagram schematically illustrating other transmission characteristics of the cut filter according to the second embodiment.

The cut filter 58 may have other transmission characteristics. FIG. 15B is a diagram schematically illustrating other transmission characteristics of the cut filter 58.

As illustrated in FIG. 15B, similarly to FIG. 15A, the cut filter 58 shields most of light of a short wavelength band and transmits therethrough light of a wavelength band longer than this short wavelength band of the light that is mostly shielded. Specifically, the cut filter 58 shields most of light of a shorter wavelength band less than any wavelength of 430 nm to 470 nm including the wavelength band of the narrow band light and transmits therethrough light of the wavelength band longer than this shorter wavelength band of the light that is mostly shielded. For example, as represented by the polygonal line $L_{NG}$ and the polygonal line $L_{PDD}$, the cut filter 58 transmits therethrough the fluorescence of AGEs produced by heat treatment and the fluorescence of 5-ALA.

Outline of Each Observation Mode

Outlines of observation modes implemented by the endoscope system 1A will be described next. The description will hereinafter be made in the order, an agent fluorescence observation mode, a heat treatment observation mode, and a normal light observation mode.

Outline of Agent Fluorescence Observation Mode

The agent fluorescence observation mode will be described first. FIG. 16 is a diagram schematically illustrating principles of observation in the agent fluorescence observation mode.

As represented by a graph G1 in FIG. 16, firstly, under control by the control device 9, the light source device 3 causes the second light source portion 32 to emit light and thereby causes narrow band light (excitation light of 415 nm) to be emitted to body tissue O1 of a subject to which an agent (5-ALA) has been administered. In this case, at least fluorescence WF1 excited in the body tissue O1 of the subject is input to the R pixels. Furthermore, reflected light and returned light (hereinafter, simply referred to as "reflected light W1") including plural components that have been reflected are shielded and reduced in intensity by the cut filter 58, and part of components longer in wavelength than this reflected light W1 that is mostly shielded is input to the imaging element 53 without being reduced in intensity.

More specifically, as represented by a polygonal line $L_F$ in a graph G2 in FIG. 16, the cut filter 58 shields most of reflected light W1 to be incident on the R pixels, the reflected light W1 having a short wavelength band including the wavelength band of the narrow band light, and transmits therethrough light of a wavelength band longer than this short wavelength band of the light that is mostly shielded. Furthermore, as represented by the graph G2 in FIG. 16, the cut filter 58 transmits therethrough fluorescence (fluorescence WF1) generated by excitation in the body tissue O1 (an agent region). As a result, the reflected light W1 that has been reduced in intensity and the fluorescence WF1 are input to each of the R pixels and B pixels.

Next, as represented by a graph G3 of transmission characteristics in FIG. 16, the R pixels, G pixels, and B pixels have transmission characteristics (sensitivity characteristics) different from one another. Specifically, output values from the B pixels become large, the output values corresponding to amounts of the reflected light W1 received, because the B pixels have sensitivity to the reflected light W1 of the narrow band light. Furthermore, output values from the R pixels become small because fluorescence is a minute reaction although the R pixels have sensitivity to the fluorescence WF1.

Thereafter, the image processing unit 93 obtains image data (RAW data) from the imaging element 53 of the endoscope camera head 5A and generates an agent fluorescence image (a pseudocolor image) by performing image processing of color component signals (pixel values) from each of the R pixels and B pixels included in the image data obtained. In this case, the color components signals from the R pixels include fluorescence information from the agent. Furthermore, the color components signals from the B pixels include background information from the body tissue O1 of the subject. Therefore, the image processing unit 93 executes processing similar to that of the first embodiment described above to generate the agent fluorescence image. Specifically, the image processing unit 93 generates the agent fluorescence image (pseudocolor image) by executing demosaicing processing, processing of calculating an intensity ratio for each pixel, processing of determining a fluorescence region and a background region, and image processing with parameters different from each other for each of color component signals (pixel values) of pixels positioned in the fluorescence region and color component signals (pixel values) of pixels positioned in the background region. The image processing unit 93 then outputs the agent fluorescence image to the display device 7. The fluorescence region is a region where fluorescence information is dominant over background information. The background region refers to a region where background information is dominant over fluorescence information. Specifically, in a case where an intensity ratio between a reflected light component signal corresponding to background information included in a pixel and a fluorescent component signal corresponding to fluorescence information included in the pixel is equal to or larger than a predetermined threshold (for example, 0.5), the image processing unit 93 determines that the pixel is of the fluorescence region, and in a case where the intensity ratio is less than the predetermined threshold, the image processing unit 93 determines that the pixel is of the background region.

Accordingly, in the agent fluorescence observation mode, a fluorescence region from an agent is able to be displayed in an enhanced manner, the fluorescence region being difficult to be visually recognized by use of white light (normal light).

Outline of Heat Treatment Observation Mode

Figure 17:
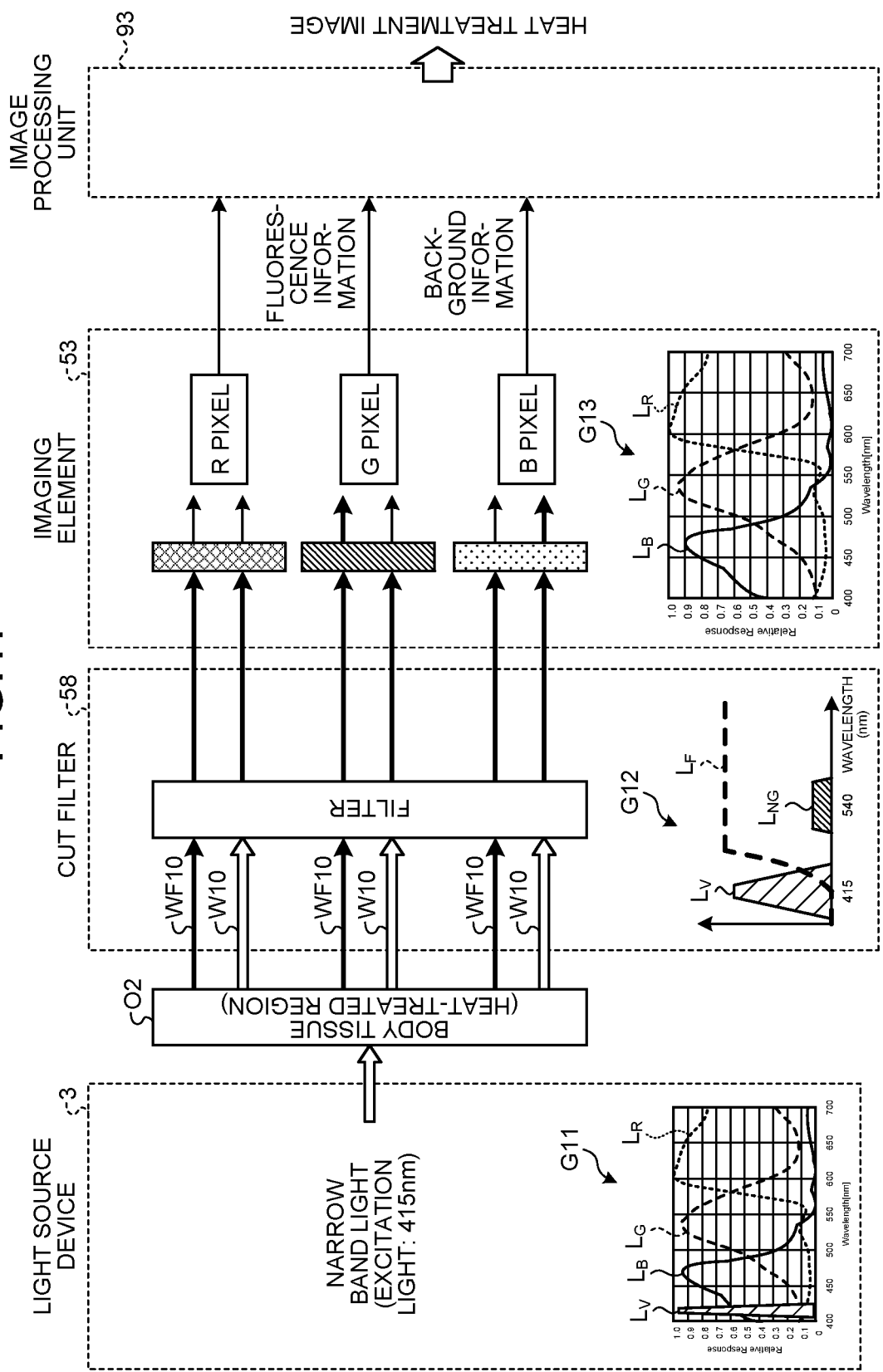
FIG. 17 is a diagram schematically illustrating principles of observation in a heat treatment observation mode according to the second embodiment.

The heat treatment observation mode will be described next. FIG. 17 is a diagram schematically illustrating principles of observation in the heat treatment observation mode.

As represented by a graph G11 in FIG. 17, firstly, under control by the control device 9, the light source device 3 emits narrow band light that is excitation light (with a central wavelength of 415 nm) to body tissue O2 (a heat-treated region) of a subject, by causing the second light source portion 32 to emit light, the body tissue O2 having been heat-treated by means of, for example, an energy device. In this case, as represented by a graph G12 in FIG. 17, at least reflected light (hereinafter, simply referred to as "reflected light W10") including components of narrow band light and returned light reflected by the body tissue O2 (heat-treated region) is shielded and reduced in intensity by the cut filter 58, and part of components longer in wavelength than this reflected light W10 that is mostly shielded is input to the imaging element 53 without being reduced in intensity.

More specifically, as represented by the graph G12 in FIG. 17, the cut filter shields most of the reflected light W10 to be incident on the G pixels and having a short wavelength band including the wavelength band of the narrow band light and transmits therethrough light of a wavelength band longer than this short wavelength band of the reflected light W10 that is mostly shielded. Furthermore, as represented by the graph G12 in FIG. 17, the cut filter 58 transmits therethrough fluorescence (WF10) resulting from autofluorescence of AGEs in the body tissue O2 (heat-treated region). Therefore, the reflected light W10 reduced in intensity and fluorescence (WF10) are input to each of the R pixels, G pixels, and B pixels.

Furthermore, as represented by a polygonal line $L_{NG}$ for fluorescence in the graph G12 in FIG. 17, the G pixels have sensitivity to fluorescence, but because this fluorescence is a minute reaction, their output values become small.

Thereafter, the image processing unit 93 obtains image data (RAW data) from the imaging element 53 of the endoscope camera head 5A, and generates a pseudocolor image (a heat treatment fluorescence image) by performing image processing of signal values from the G pixels and B pixels, the signal values being included in the image data obtained. In this case, the signal values from the G pixels include fluorescence information generated from the heat-treated region. Furthermore, the signal values from the B pixels include background information from the body tissue O2 of the subject, the body tissue O2 including the heat-treated region. Therefore, the image processing unit 93 executes processing similar to that of the first embodiment described above to generate a heat treatment image. Specifically, the image processing unit 93 generates the heat treatment image (pseudocolor image) by executing demosaicing processing, processing of calculating an intensity ratio for each pixel, processing of determining a fluorescence region and a background region, and image processing with parameters different from each other for each of color component signals (pixel values) of pixels positioned in the fluorescence region and color component signals (pixel values) of pixels positioned in the background region. The image processing unit 93 then outputs the heat treatment image to the display device 7. The fluorescence region is a region where fluorescence information is dominant over background information. Furthermore, the background region refers to a region where background information is dominant over fluorescence information. Specifically, in a case where an intensity ratio between a reflected light component signal corresponding to background information included in a pixel and a fluorescent component signal corresponding to fluorescence information included in the pixel is equal to or larger than a predetermined threshold (for example, 0.5), the image processing unit 93 determines that the pixel is of the fluorescence region, and in a case where the intensity ratio is less than the predetermined threshold, the image processing unit 93 determines that the pixel is of the background region.

Accordingly, the heat treatment observation mode facilitates observation of the body tissue O2 (heat-treated region) that is heat-treated by the energy device, for example.

Outline of Normal Light Observation Mode

The normal light observation mode will be described next. FIG. 18 is a diagram schematically illustrating principles of observation in the normal light observation mode.

As illustrated in FIG. 18, firstly, under control by the control device 9, the light source device 3 emits white light W3 to body tissue O3 of a subject by causing the first light source portion 31 to emit light. In this case, part of reflected light and returned light that have been reflected by the body tissue O3 (hereinafter, simply referred to as "reflected light WR30, reflected light WG30, and reflected light WB30") is shielded by the cut filter 58 and the rest enters the imaging element 53. Specifically, as illustrated in FIG. 18, the cut filter 58 shields reflected light of a short wavelength band including the wavelength band of the narrow band light. Therefore, as illustrated in FIG. 18, a blue wavelength band light component incident on the B pixels is less than that in a state without the cut filter 58 arranged in the system.

Next, the image processing unit 93 obtains image data (RAW data) from the imaging element 53 of the endoscope camera head 5A, and generates a white light image by performing image processing of signal values from the R pixels, G pixels, and B pixels, the signal values being included in the image data obtained. In this case, because the blue component included in the image data is less than that in conventional white light observation, the image processing unit 93 performs white balance adjustment processing of adjusting white balance to make the ratio of the red component, green component, and blue component constant.

As described above, in the normal light observation mode, even in a case where the cut filter 58 has been arranged, a natural white image is able to be observed.

That is, the endoscope system 1A performs processing similar to that of the first embodiment described above to determine a background region and a fluorescence region in each of the agent fluorescence observation mode and the heat treatment observation mode, and uses image processing parameters different from each other for the background region and fluorescence region to thereby generate an agent fluorescence image or a heat treatment image and cause the agent fluorescence image or the heat treatment image to be displayed by the display device 7, the agent fluorescence image or the heat treatment image having the fluorescence region enhanced in relation to the background region.

The second embodiment described above has effects similar to those of the first embodiment described above, and also enables fluorescence to be prevented from being buried in reflected light and returned light reflected by body tissue, the fluorescence being from a heat-treated region, because the second embodiment has the cut filter 58 provided therein, the cut filter 58 serving as an optical element.

Third Embodiment

A third embodiment will be described next. An endoscope system according to the third embodiment has the same configuration as the above described endoscope systems according to the first and second embodiments, but executes processing different from that by these endoscope systems. Specifically, in the above described first or second embodiment, the control unit sets, according to the observation mode set correspondingly to a mode signal input from the input unit, the intensity ratio of color component signals to be calculated by the calculating unit, but in this third embodiment, the control unit sets the intensity ratio of color component signals to be calculated by the calculating unit according to the type of the endoscope camera head connected to the control device. The processing executed by the endoscope system according to the third embodiment will thus be described hereinafter. The same reference signs will be assigned to components that are the same as those of the above described endoscope system according to the first embodiment, and detailed description of these components will thus be omitted.

Processing by Endoscope System

Figure 19:
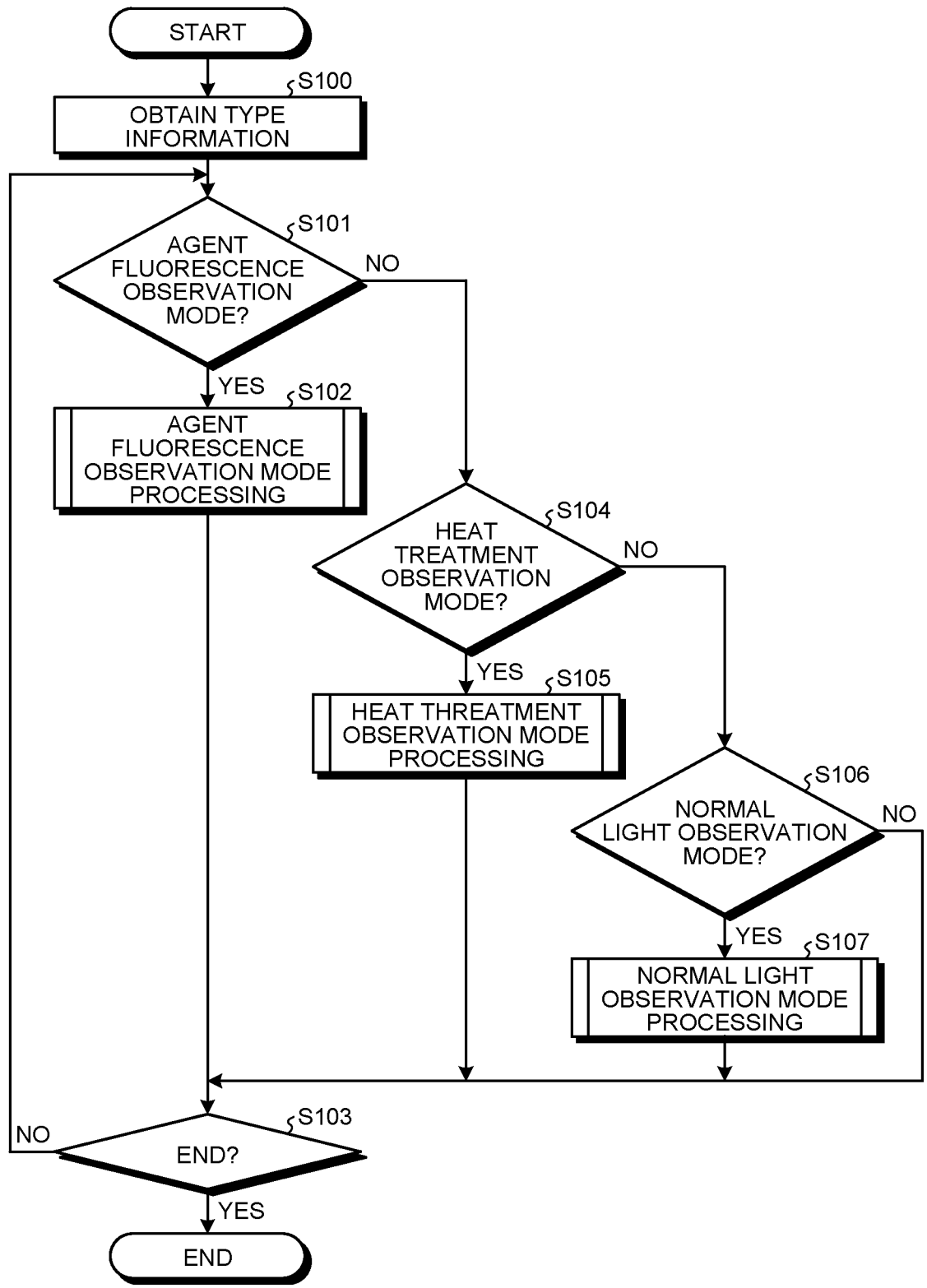
FIG. 19 is a flowchart illustrating an outline of processing executed by an endoscope system according to a third embodiment.

FIG. 19 is a flowchart illustrating an outline of processing executed by the endoscope system according to the third embodiment. In FIG. 19, any one of the above described endoscope camera head 5 according to the first embodiment and the above described endoscope camera head 5A according to the second embodiment is connected. That is, in this third embodiment, the endoscope camera head 5 functions as a first medical imaging device, and the endoscope camera head 5A functions as a second medical imaging device. Furthermore, any one of the endoscope camera head 5 and the endoscope camera head 5A will hereinafter be simply referred to as the endoscope camera head.

As illustrated in FIG. 19, firstly, the control unit 96 obtains type information that have been recorded in the imaging recording unit 56 of the endoscope camera head connected to the control device 9, the type information indicating the type of the endoscope camera head (Step S100).

Subsequently, on the basis of the type information obtained at Step S101, the control unit 96 determines whether or not the endoscope camera head connected to the control device 9 is the endoscope camera head 5 (first medical imaging device) that is capable of implementing the agent fluorescence observation mode (Step S101). In a case where the control unit 96 has determined that the endoscope camera head connected to the control device 9 is the endoscope camera head 5 (first medical imaging device) that is capable of implementing the agent fluorescence observation mode (Step S101: Yes), the endoscope system 1 proceeds to Step S102 described later. On the contrary, in a case where the control unit 96 has determined that the endoscope camera head connected to the control device 9 is not the endoscope camera head 5 (first medical imaging device) that is capable of implementing the agent fluorescence observation mode (Step S101: No), the endoscope system 1 proceeds to Step S104 described later.

Step S102 and Step S103 respectively correspond to Step S2 and Step S3 in FIG. 8 described above.

At Step S104, on the basis of the type information obtained at Step S100, the control unit 96 determines whether or not the endoscope camera head connected to the control device 9 is the endoscope camera head 5A (second medical imaging device) that is capable of implementing the heat treatment observation mode. In a case where the control unit 96 has determined that the endoscope camera head connected to the control device 9 is the endoscope camera head 5A (second medical imaging device) that is capable of implementing the heat treatment observation mode (Step S104: Yes), the endoscope system 1 proceeds to Step S105 described later. On the contrary, in a case where the control unit 96 has determined that the endoscope camera head connected to the control device 9 is not the endoscope camera head 5A (second medical imaging device) that is capable of implementing the heat treatment observation mode (Step S104: No), the endoscope system 1 proceeds to Step S106 described later.

Step S105 to Step S107 respectively correspond to Step S5 to Step S7 in FIG. 8 described above.

The third embodiment described above enables image processing with parameters according to an observation mode to be implemented by the endoscope camera head connected to the control device 9 and enables, similarly to the above described first and second embodiments, improvement in visibility of fluorescence, because the control unit 96 sets, on the basis of type information indicating the type of the endoscope camera head connected to the control device 9, color component signals for intensity ratios to be calculated by the calculating unit 932.

Fourth Embodiment

Figure 20:
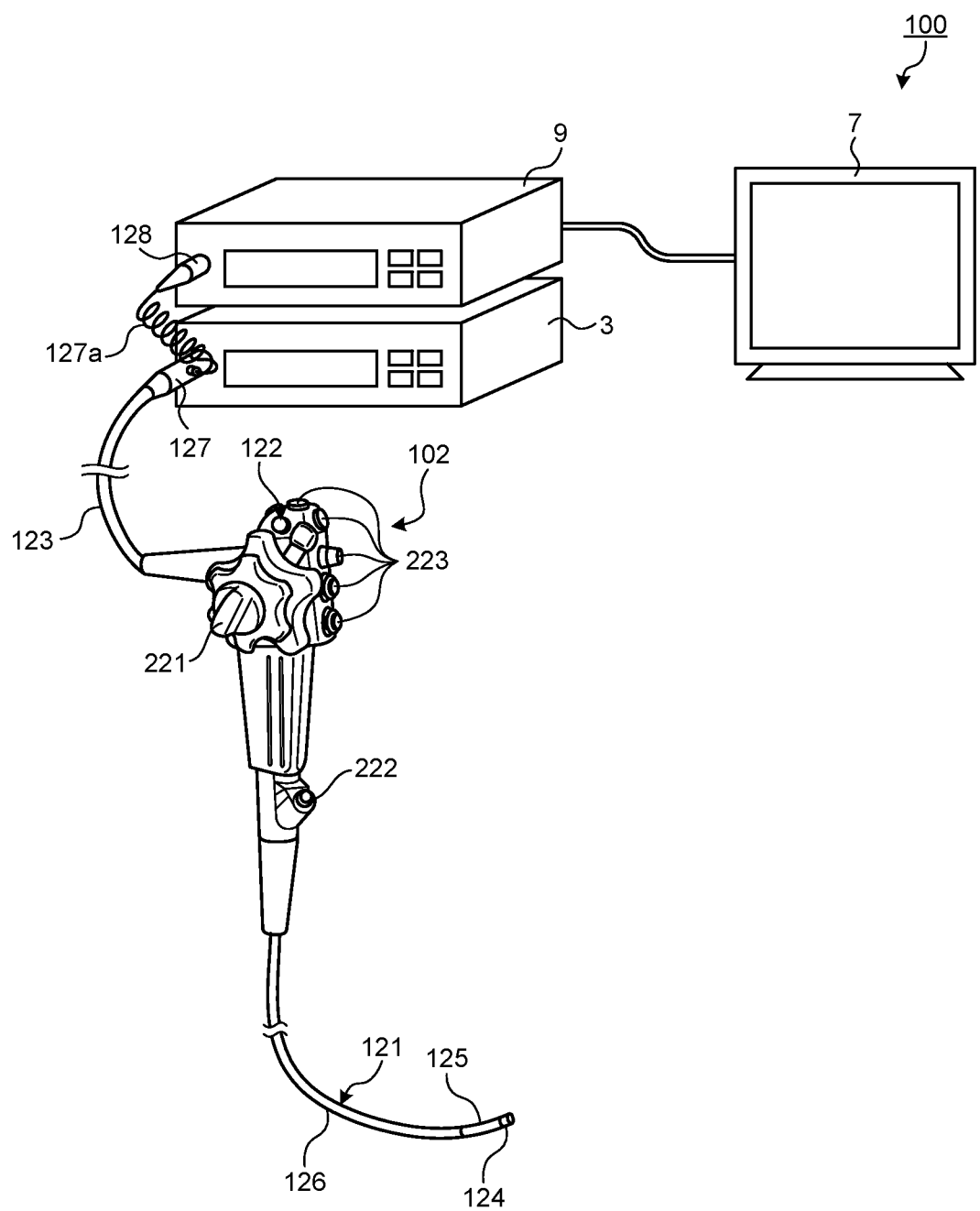
FIG. 20 is a diagram illustrating a schematic configuration of an endoscope system according to a fourth embodiment.
Figure 21:
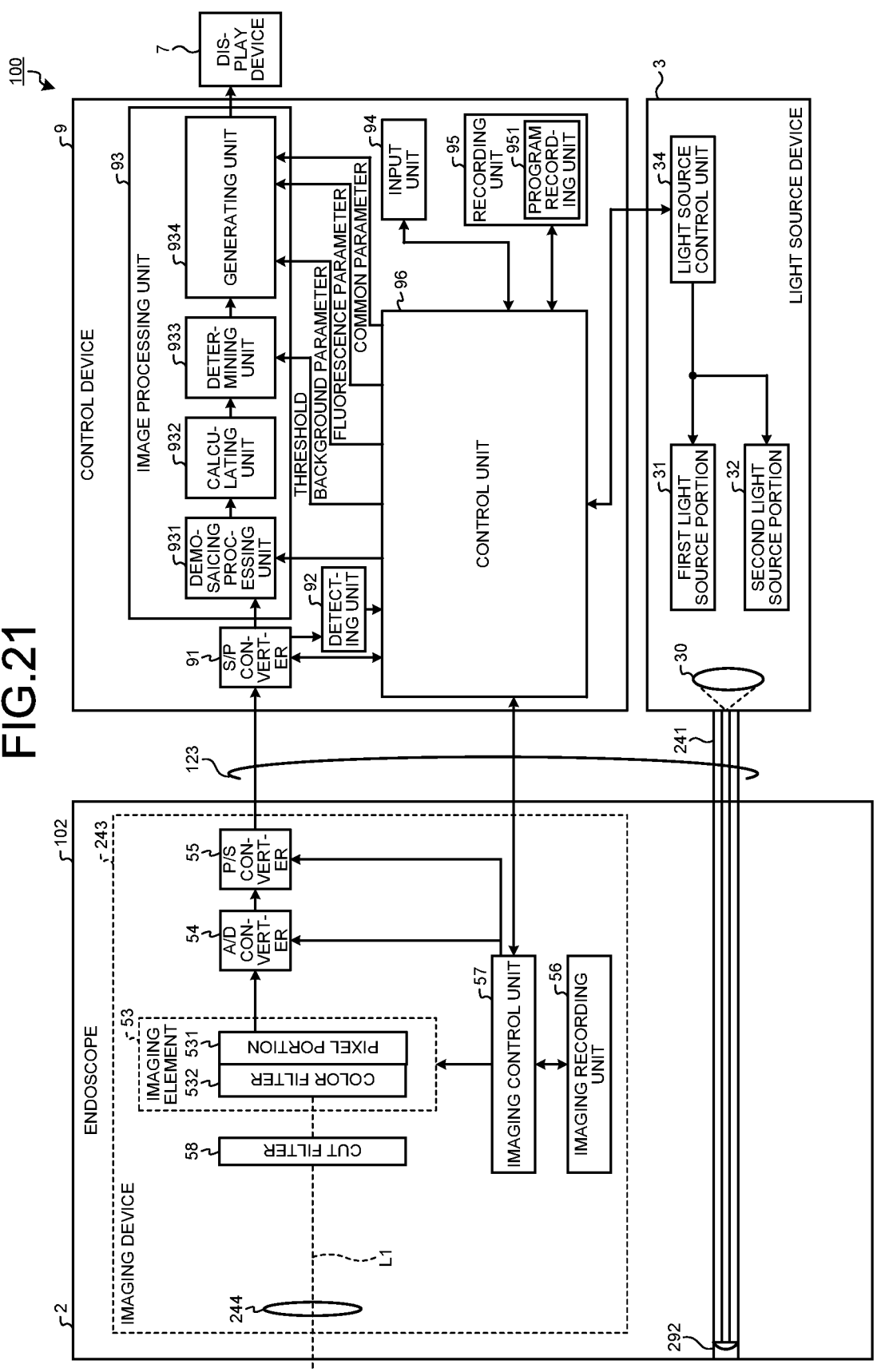
FIG. 21 is a block diagram illustrating a functional configuration of main parts of the endoscope system according to the fourth embodiment.

A fourth embodiment will be described next. The first to third embodiments described above are each related to an endoscope system including a rigid endoscope, but an endoscope system including a flexible endoscope will be described with respect to this fourth embodiment. The endoscope system according to the fourth embodiment will be described hereinafter. The same reference signs will be assigned to components of the fourth embodiment that are the same as those of the above described endoscope system 1 according to the first embodiment, and detailed description of these components will thus be omitted.
Configuration of Endoscope System FIG. 20 is a diagram illustrating a schematic configuration of the endoscope system according to the fourth embodiment. FIG. 21 is a block diagram illustrating a functional configuration of main parts of the endoscope system according to the fourth embodiment.

In an endoscope system 100 illustrated in FIG. 20 and FIG. 21, an image of the interior of the body of a subject, such as a patient, is captured by insertion into the subject, and a display image based on data on the image captured is displayed by the display device 7. By observing the display image displayed by the display device 7, an operating surgeon, such as a medical doctor, examines any presence and/or a state of an abnormal region having a site to be examined captured therein, the site being, for example, a bleeding site, a tumor site, and/or an abnormal site. Furthermore, the operating surgeon, such as a medical doctor, performs treatment of the subject by inserting a treatment tool, such as an energy device, into the body of the subject via a treatment tool channel of an endoscope. The endoscope system 100 includes, in addition to the light source device 3, the display device 7, and the control device 9 described above, an endoscope 102.
Configuration of Endoscope The following description is related to a configuration of the endoscope 102. The endoscope 102 generates image data by capturing an image of the interior of the body of a subject and outputs the image data generated, to the control device 9. The endoscope 102 includes an operating unit 122 and a universal cord 123.

An insertion portion 121 has flexibility and is elongated. The insertion portion 121 includes: a distal end portion 124 having, built therein, an imaging device described later; a bending portion 125 that includes plural bending pieces and is bendable; and a flexible tube portion 126 that is connected to a proximal end of the bending portion 125, has flexibility, and is elongated.

The distal end portion 124 is formed by use of, for example, glass fiber. The distal end portion 124 includes: a light guide 241 forming a light guiding path for light supplied from the light source device 3; an illumination lens 242 provided at a distal end of the light guide 241; and an imaging device 243.

The imaging device 243 includes an optical system 244 for condensing light, and the above described imaging element 53, cut filter 58, A/D converter 54, P/S converter 55, imaging recording unit 56, and imaging control unit 57 according to the first embodiment. In this fourth embodiment, the imaging device 243 functions as a medical imaging device.

The universal cord 123 has, built therein, at least the light guide 241 and an assembly cable having one or plural cables bundled together. The assembly cable includes signal lines for transmitting and receiving signals between: the endoscope 102 and light source device 3; and the control device 9. These signal lines include a signal line for transmitting and receiving setting data, a signal line for transmitting and receiving a captured image (image data), and a signal line for transmitting and receiving a driving timing signal for driving the imaging element 53. The universal cord 123 has a connector 127 that is attachable to and detachable from the light source device 3. A coil cable 127a that is coil-shaped extends from the connector 127. A connector 128 attachable to and detachable from the control device 9 is provided at an extended end of the coil cable 127a.

The endoscope system 100 configured as described above performs processing similar to that by the above described endoscope system 1 according to the first embodiment.

The fourth embodiment described above has effects similar to those of the first embodiment described above, and also enables reduction in diameter of the insertion portion 121 because both narrow band light observation and observation of fluorescence generated by heat treatment with, for example, an energy device are able to be conducted by means of just the single imaging element 53.

Fifth Embodiment

Figure 22:
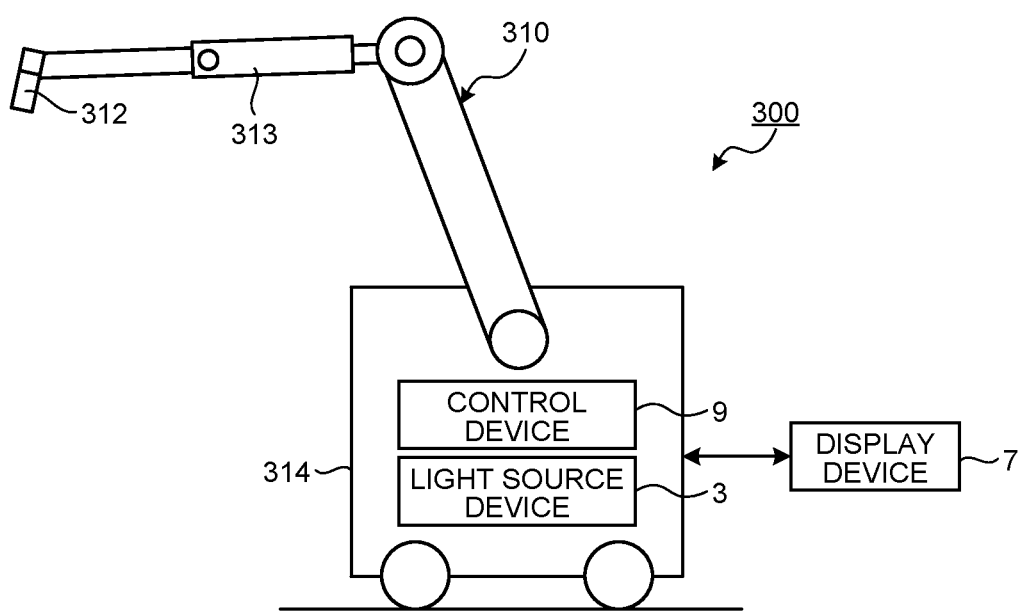
FIG. 22 is a diagram illustrating a schematic configuration of a surgical microscope system according to a fifth embodiment.

A fifth embodiment will be described next. Endoscope systems have been described above with respect to the first to fourth embodiments, but application to a surgical microscope system will be described with respect to the fifth embodiment. The same reference signs will be assigned to components of the fifth embodiment that are the same as those of the above described endoscope system 1 according to the first embodiment, and detailed description of these components will thus be omitted.
Configuration of Surgical Microscope System FIG. 22 is a diagram illustrating a schematic configuration of the surgical microscope system according to the fifth embodiment. A surgical microscope system 300 illustrated in FIG. 22 includes: a microscope device 310 that is a medical imaging device that obtains, by imaging, an image for observation of a subject; and the display device 7. The display device 7 and the microscope device 310 may be configured integrally with each other.

The microscope device 310 includes: a microscope unit 312 that captures an enlarged image of a microscopic site in a subject; a supporting unit 313 that is connected to a proximal end portion of the microscope unit 312 and includes an arm that supports the microscope unit 312 rotatably; and a base unit 314 that holds a proximal end portion of the supporting unit 313 rotatably and is capable of moving on a floor surface. The base unit 314 includes: the light source device 3 that generates, for example, white light and narrow band light to be emitted to a subject from the microscope device 310; and the control device 9 that controls operation of the surgical microscope system 300. The light source device 3 and the control device 9 both have at least the same configurations as those of the first embodiment described above. Specifically, the light source device 3 includes the condenser lens 30, the first light source portion 31, the second light source portion 32, and the light source control unit 34. The control device 9 includes the S/P converter 91, the image processing unit 93, the input unit 94, the recording unit 95, and the control unit 96. Instead of being provided movably on the floor surface, the base unit 314 may be configured to support the supporting unit 313 by being be fixed to, for example, a ceiling or a wall surface.

The microscope unit 312 is, for example, cylindrical, and has therein the medical imaging device described above. Specifically, the medical imaging device includes the same configuration as that of the above described endoscope camera head 5 according to the first embodiment. For example, the microscope unit 312 includes the optical system 51, the drive unit 52, the imaging element 53, the A/D converter 54, the P/S converter 55, the imaging recording unit 56, the imaging control unit 57, and the cut filter 58. Furthermore, a switch that receives input of an operation instruction for the microscope device 310 is provided on a side surface of the microscope unit 312. A cover glass (not illustrated in the drawings) that protects the interior of the microscope unit 312 is provided on the plane of an opening at a lower end of the microscope unit 312.

In the surgical microscope system 300 configured as described above, the microscope unit 312 is moved, a zooming operation is performed, and/or illumination light is changed, by a user, such as an operating surgeon, while the user operates any of various switches in a state where the microscope unit 312 is being held by the user. The microscope unit 312 preferably has an elongated shape extending in an observation direction so that it is easy for the user to hold the microscope unit 312 and change the field of view direction. Therefore, the microscope unit 312 may be not cylindrical, and may have, for example, a polygonal prism shape.

The above described surgical microscope system 300 according to the fifth embodiment also achieves effects similar to those of the above described first embodiment and additionally enables downsizing of the microscope unit 312.

Other Embodiments

Various embodiments may be formed by combination, as appropriate, of plural components disclosed with respect to the above described medical observation systems according to the first to fourth embodiments of the present disclosure. For example, some of the components described with respect to the medical observation system/systems according to any of the above described embodiments of the present disclosure may be eliminated. Furthermore, any components described with respect to the medical observation system/systems according to any of the above described embodiments of the present disclosure may be combined as appropriate.

Furthermore, the "units" described above with respect to the medical observation systems according to the first to fourth embodiments of the present disclosure may be read as "means" or "circuits". For example, the control unit may be read as a control means or a control circuit.

In the description of the flowcharts in this specification, the context of the processing among the steps is disclosed by use of expressions, such as "firstly", "thereafter", and "subsequently", but sequences in the processing needed for implementation of the disclosure are not uniquely defined by these expressions. That is, the sequences in the processing in the flowcharts described in this specification may be modified as far as no contradiction arises from the modification.

Some of embodiments of the present application have been described hereinbefore in detail on the basis of the drawings, but these are just examples. The disclosure may be implemented in various other modes modified or improved on the basis of the modes described through the present disclosure and knowledge of those skilled in the art.

The present disclosure achieves an effect of enabling improved visibility of fluorescence.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image processing device, comprising a processor comprising hardware, the processor being configured to:
   obtain image data generated by imaging of reflected light and fluorescence, the reflected light being from body tissue irradiated with narrow band light, the fluorescence being from an observation target that emits fluorescence by irradiation of the body tissue with the narrow band light;
   generate, based on the obtained image data, a captured image including color component signals including:
      a red component signal representing a red component;
      a green component signal representing a green component; and
      a blue component signal representing a blue component;
   calculate an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light;
   determine, based on the calculated intensity ratio in the pixel of the captured image, a fluorescence region and a background region in the captured image; and
   generate a fluorescence image by performing, based on a result of the determination, image processing with parameters different from each other for color component signals in pixels positioned in the fluorescence region and color component signals in pixels positioned in the background region.

2. The medical image processing device according to claim 1, wherein the observation target is an advanced glycation end product produced by performing a heat treatment on the body tissue.

3. The medical image processing device according to claim 2, wherein:
   the fluorescent component signal is the green component signal; and
   the reflected light component signal is the blue component signal.

4. The medical image processing device according to claim 2, wherein the advanced glycation end product is generated by the heat treatment by an energy device.

5. The medical image processing device according to claim 1, wherein the observation target is an agent including a fluorescent substance.

6. The medical image processing device according to claim 5, wherein:
the fluorescent component signal is the red component signal; and
the reflected light component signal is the blue component signal.

7. The medical image processing device according to claim 1, wherein the image processing performed by the processor is gain adjustment processing where gains for the color component signals of the pixels positioned in the fluorescence region are made larger than gains for the color component signals of the pixels positioned in the background region.

8. The medical image processing device according to claim 1, wherein the processor is further configured to:
detect brightness of the captured image;
set, based on the detected brightness, a threshold for determining the fluorescence region and the background region; and
determine, based on the set threshold and on the intensity ratio, the fluorescence region and the background region.

9. The medical image processing device according to claim 8, wherein the processor is further configured to set, based on type information indicating a type of a medical imaging device connectable to the medical image processing device, the fluorescent component signal and the reflected light component signal for the intensity ratio.

10. The medical image processing device according to claim 9, wherein:
the medical image processing device is capable of being connected to either a first medical imaging device or a second medical imaging device;
the first medical imaging device comprises:
an imaging element including:
a pixel portion including plural pixels arranged in a two-dimensional matrix; and
a color filter including red filters, green filters, and blue filters provided on light receiving surfaces of the plural pixels, each of the light receiving surfaces including any one filter of the red, green, and blue filters on each of the light receiving surfaces;
the second medical imaging device comprises:
an imaging element including:
a pixel portion including plural pixels arranged in a two-dimensional matrix; and
a color filter including red filters, green filters, and blue filters provided on light receiving surfaces of the plural pixels, each of the light receiving surfaces including any one filter of the red, green, and blue filters on each of the light receiving surfaces;
an optical system configured to form a subject image on a light receiving surface of the imaging element; and
a cut filter provided on an optical path of the imaging element and optical system, the cut filter being configured to shield part of light of a shorter wavelength band including a wavelength band of the narrow band light, and transmit therethrough light of a wavelength band longer than a wavelength band of the light that is shielded; and the processor is configured to set, based on the type information of any one of the first medical imaging device and the second medical imaging device, the fluorescent component signal and the reflected light component signal for the intensity ratio.

11. The medical image processing device according to claim 10, wherein the processor is further configured to:
determine, based on the type information, whether or not the first medical imaging device or the second medical imaging device has been connected to the medical image processing device;
cause the intensity ratio to be calculated by use of the red component signal and the blue component signal when it is determined that the first medical imaging device has been connected to the medical image processing device; and
cause the intensity ratio to be calculated by use of the green component signal and the blue component signal when it is determined that the second medical imaging device has been connected to the medical image processing device.

12. The medical image processing device according to claim 11, wherein the fluorescence has a wavelength band of 500 nm to 640 nm.

13. The medical image processing device according to claim 12, wherein:
the narrow band light has a wavelength band of 390 nm to 470 nm; and
the cut filter shields part of light of a wavelength band shorter than 470 nm.

14. A medical imaging device comprising:
an imaging element including:
a pixel portion including plural pixels arranged in a two-dimensional matrix; and
a color filter including red filters, green filters, and blue filters that are provided on light receiving surfaces of the plural pixels, each of the light receiving surfaces including any one filter of the red, green, and blue filters on plural pixels, each of the light receiving surfaces;
an optical system configured to forms a subject image on a light receiving surface of the imaging element; and
a cut filter provided on an optical path of the imaging element and optical system,
wherein:
the imaging element is configured to generate image data by imaging at least one of:
reflected light from body tissue irradiated with narrow band light shorter in wavelength; and
fluorescence from an advanced glycation end product produced by performing a heat treatment on the body tissue; and
the cut filter is configured to shield part of light of a shorter wavelength band including a wavelength band of the narrow band light, and transmit therethrough light of a wavelength band longer than a wavelength band of the light that is shielded.

15. A medical observation system comprising:
a light source configured to emit narrow band light;
a medical imaging device configured to generate image data; and
a medical image processing device comprising a processor comprising hardware, the processor being configured to:
obtain image data generated by imaging of reflected light and fluorescence, the reflected light being from body tissue irradiated with narrow band light, the fluorescence being from an observation target that emits fluorescence by irradiation of the body tissue with the narrow band light;

generate, based on the obtained image data, a captured image including color component signals including:
a red component signal representing a red component;
a green component signal representing a green component; and
a blue component signal representing a blue component;

calculate an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light;

determine, based on the calculated intensity ratio in the pixel of the captured image, a fluorescence region and a background region in the captured image; and generate a fluorescence image by performing, based on a result of the determination, image processing with parameters different from each other for color component signals in pixels positioned in the fluorescence region and color component signals in pixels positioned in the background region.

16. The medical observation system according to claim 15, further comprising:
an insertion portion configured to be inserted into a subject, the insertion portion including an optical system configured to condense the reflected light and the fluorescence,
wherein the insertion portion is attachable to and detachable from the medical imaging device.

17. The medical observation system according to claim 15, further comprising:
an endoscope including an insertion portion including a distal end portion configured to be inserted into the subject,
wherein the medical imaging device is provided at the distal end portion.

18. The medical observation system according to claim 15, further comprising:
a support configured to support the medical imaging device rotatably; and
a base configured to hold a proximal end portion of the support rotatably, the base being configured to move on a floor surface.

19. An image processing method comprising:
obtaining image data generated by imaging of reflected light and fluorescence, the reflected light being from body tissue irradiated with narrow band light, the fluorescence being from an observation target that emits fluorescence by irradiation of the body tissue with the narrow band light;
generating, based on the obtained image data, a captured image including color component signals including:
a red component signal representing a red component;
a green component signal representing a green component; and
a blue component signal representing a blue component;

calculating an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light;

determining, based on the calculated intensity ratio in the pixel of the captured image, a fluorescence region and a background region in the captured image; and generating a fluorescence image by performing, based on a result of the determining, image processing with parameters different from each other for color component signals in pixels positioned in the fluorescence region and color component signals in pixels positioned in the background region.

20. A non-transitory computer-readable recording medium with an executable program stored thereon, the program causing a medical image processing device to:
obtain image data generated by imaging of reflected light and fluorescence, the reflected light being from body tissue irradiated with narrow band light, the fluorescence being from an observation target that emits fluorescence by irradiation of the body tissue with the narrow band light;

generate, based on the obtained image data, a captured image including color component signals including:
a red component signal representing a red component;
a green component signal representing a green component; and
a blue component signal representing a blue component;

calculate an intensity ratio between a fluorescent component signal and a reflected light component signal in a pixel of the captured image, the fluorescent component signal being one of the red component signal, the green component signal, and the blue component signal and being highly sensitive to the fluorescence from the observation target, the reflected light component signal being another one of the red component signal, the green component signal, and the blue component signal and being highly sensitive to the reflected light from the body tissue irradiated with the narrow band light;

determine, based on the calculated intensity ratio in the pixel of the captured image, a fluorescence region and a background region in the captured image; and generate a fluorescence image by performing, based on a result of the determination, image processing with parameters different from each other for color component signals in pixels positioned in the fluorescence region and color component signals in pixels positioned in the background region.

* * * * *